(12) United States Patent
Tamatani et al.

(10) Patent No.: US 8,466,238 B2
(45) Date of Patent: Jun. 18, 2013

(54) LATENT CURING AGENTS, EPOXY RESIN COMPOSITIONS CONTAINING THE SAME, SEALING MATERIALS, AND ORGANIC EL DISPLAYS

(75) Inventors: Hiroaki Tamatani, Mobara (JP); Mitsuaki Chida, Mobara (JP); Yugo Yamamoto, Chiba (JP); Yuichi Ito, Ichihara (JP); Takashi Nakano, Sodegaura (JP); Naritoshi Yoshimura, Ichihara (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 518 days.

(21) Appl. No.: 12/681,271

(22) PCT Filed: Dec. 26, 2008

(86) PCT No.: PCT/JP2008/004016
§ 371 (c)(1),
(2), (4) Date: Apr. 1, 2010

(87) PCT Pub. No.: WO2009/084229
PCT Pub. Date: Jul. 9, 2009

(65) Prior Publication Data
US 2010/0253213 A1     Oct. 7, 2010

(30) Foreign Application Priority Data
Dec. 28, 2007  (JP) ................ 2007-340785

(51) Int. Cl.
C07C 243/14  (2006.01)
C07D 211/98  (2006.01)
C08G 59/50   (2006.01)
C08G 59/58   (2006.01)
C08L 63/00   (2006.01)
C08L 63/02   (2006.01)

(52) U.S. Cl.
USPC ........ 525/523; 525/330.5; 525/420; 525/453; 525/533; 525/535; 528/113; 528/118; 528/121; 528/122; 528/124; 546/224; 546/244; 564/454

(58) Field of Classification Search
None
See application file for complete search history.

(56) References Cited

U.S. PATENT DOCUMENTS

| 3,888,827 A * | 6/1975 | Matueda et al. .............. 528/113 |
| 3,985,807 A | 10/1976 | Grimm et al. |
| 4,005,055 A | 1/1977 | Miron et al. |
| 5,393,805 A * | 2/1995 | Koyama et al. .............. 523/400 |
| 5,734,082 A | 3/1998 | Hogan, Jr. et al. |
| 6,492,438 B1 * | 12/2002 | Nomura ....................... 523/466 |

FOREIGN PATENT DOCUMENTS

| JP | 53-57258 A | 5/1978 |
| JP | 61-231020 A * | 10/1986 |
| JP | 10-139748 A | 5/1998 |
| JP | 10-507753 A | 7/1998 |
| JP | 2000-229927 A | 8/2000 |
| JP | 2003-96061 A | 4/2003 |
| WO | WO 96/12482 A1 | 5/1996 |
| WO | WO 02/051905 | 7/2002 |

OTHER PUBLICATIONS

Derwent accession No. 2002-691499 for PCT Publication No. WO 2002/051905 A1, Jul. 4, 2002, three pages.*
International Search Report (PCT/ISA/210) dated Mar. 10, 2009.

* cited by examiner

*Primary Examiner* — Robert Sellers
(74) *Attorney, Agent, or Firm* — Buchanan Ingersoll & Rooney PC

(57) ABSTRACT

The invention aims to provide latent curing agents which exert high low-temperature curing properties when used together with ionically polymerizable compounds and which exhibit high storage stability at room temperature. Latent curing agents for ionically polymerizable compounds which agents each contain a hydroxyl-free amine imide compound having an N—N bond energy of 100 to 210 kJ/mol as determined by B3LYP functional theory method.

8 Claims, 1 Drawing Sheet

TABLE 1-1

| | UNIT | EXAMPLE 1 | EXAMPLE 2 | EXAMPLE 3 | EXAMPLE 4 | EXAMPLE 5 | EXAMPLE 6 | EXAMPLE 7 | EXAMPLE 8 | EXAMPLE 9 |
|---|---|---|---|---|---|---|---|---|---|---|
| AMINE IMIDE | | COMPOUND 1 | COMPOUND 2 | COMPOUND 3 | COMPOUND 4 | COMPOUND 5 | COMPOUND 6 | COMPOUND 7 | COMPOUND 8 | COMPOUND 9 |
| LOW-TEMPERATURE CURING ABILITY (90°C/2h) | % | 62.3 | 92.3 | 76.8 | 92.1 | 90.8 | 94.2 | 94.2 | 94.4 | 89.0 |
| | | △ | ○ | △ | ○ | ○ | ○ | ○ | ○ | △ |
| ROOM TEMPERATURE STORAGE STABILITY | — | 1.3 | 1.7 | 1.6 | 1.7 | 1.7 | 1.7 | 1.6 | 1.4 | 1.5 |
| | | ○ | △ | △ | △ | △ | △ | △ | ○ | △ |
| INITIAL VISCOSITY | mPa·s | 4360 | 5640 | 6000 | 5320 | 6770 | 4770 | 4350 | 4260 | 3953 |
| N-N BOND ENERGY | kJ/mol | 206.6 | 145.5 | 173.3 | 139.2 | 140.2 | 127.8 | 111.4 | 147.9 | 174.1 |

TABLE 1-2

| | UNIT | COMPARATIVE EXAMPLE 1 | COMPARATIVE EXAMPLE 2 | COMPARATIVE EXAMPLE 3 | COMPARATIVE EXAMPLE 4 | COMPARATIVE EXAMPLE 5 | COMPARATIVE EXAMPLE 6 | COMPARATIVE EXAMPLE 7 | COMPARATIVE EXAMPLE 8 |
|---|---|---|---|---|---|---|---|---|---|
| AMINE IMIDE | | COMPOUND A | COMPOUND B | COMPOUND F | COMPOUND G | COMPOUND H | COMPOUND I | COMPOUND C | COMPOUND J |
| LOW-TEMPERATURE CURING ABILITY (90°C/2h) | % | 64.2 | 86.2 | NOT DISSOLVED (UNMEASURABLE) | | 64.3 | 49.3 | 90.0 | 87.9 |
| | | △ | △ | | | △ | × | ○ | △ |
| ROOM TEMPERATURE STORAGE STABILITY | — | 1.6 | UNMEASURABLE | — | | 2.0 | 1.6 | 3.5 | 2.8 |
| | | △ | × | | | × | △ | × | × |
| INITIAL VISCOSITY | mPa·s | 7330 | 73000 | | | 5640 | 7250 | 100000 | 100000 |
| N-N BOND ENERGY | kJ/mol | 216.1 | 174.6 | | 242.6 | 219.6 | 227.0 | 187.5 | 192.7 |

LATENT CURING AGENTS, EPOXY RESIN COMPOSITIONS CONTAINING THE SAME, SEALING MATERIALS, AND ORGANIC EL DISPLAYS

TECHNICAL FIELD

The present invention relates to a latent curing agent, an epoxy resin composition containing the same, a sealant, and an organic EL display.

BACKGROUND ART

Amine imides are known as useful compounds for sources of polymerizable compounds such as polyurethane resins and polyurea resins, as well as for curing agents, cleaners, surfactants, surface treating agents, pharmaceutical or agrochemical intermediates, etc.

Amine imides are characterized by the fact that they undergo dissociation by the cleavage of the nitrogen-nitrogen (N—N) bond in their molecular structure by heat treatment, to produce an isocyanate and a tertiary amine. The isocyanate reacts with organic compounds bearing such functional groups as hydroxyl or amino groups, and the tertiary amine is highly basic and therefore acts as a curing agent for epoxy or other resins. Because of these properties, amine imides have been utilized as, for example, latent curing agents for epoxy resins.

Dissociation of an amine imide, however, generally requires temperatures as high as 130° C. or above. This makes the compound difficult to be used as a latent curing agent for epoxy resin compositions for use as adhesions, coatings and electric/electronic materials, where curing should be effected at relatively low temperatures. Thus, demand has been growing for amine imides that can cure epoxy resin compositions at lower temperatures, i.e., offer high low-temperature curing ability.

Examples of amine imides known to be capable of curing epoxy resin compositions at lower temperatures include those having an organic group in which a hydroxyl group is bonded to a carbon atom to which a carbonyl carbon atom is bonded (see, e.g., Patent Document 1), and those having one or two hydroxyl groups in their molecular structure (see, e.g., Patent Document 2).

Patent Document 3 discloses amine imides in which an olefinic double bond is introduced to the carbonyl carbon atom of the amine imide group. Patent Document 3 also discloses amine imides having hydroxyl groups in addition to an olefinic double bond and describes that the hydroxyl groups may react with isocyanates. However, the amine imides are disclosed as being polymerizable compounds (monomers) which polymerize under anaerobic conditions, not as curing agents used to polymerize or cure other polymerizable compounds.

Patent Document 1: Japanese Patent Application Laid-Open No. 2000-229927
Patent Document 2: Japanese Patent Application Laid-Open No. 2003-096061
Patent Document 3: U.S. Pat. No. 4,005,055

DISCLOSURE OF INVENTION

Problems to be Solved by the Invention

In recent years studies have been made to make use of the above-noted features of amine imides, aiming to apply epoxy resin compositions, which contain an amine imide as a latent curing agent, to sealants for use in display devices such as liquid crystal displays and organic EL displays. There is a need for sealants which cure at temperatures as low as around 80° C. because liquid crystals and organic EL materials are susceptible to degradation by heat.

Dissociation of amine imides disclosed by Patent Documents 1 and 2, however, requires heat treatment around 100 to 120° C.; therefore, they do not dissociate by heating around 80° C. and thus cannot cure epoxy resins.

Sealants for display devices require not only a property that allows the agent to cure even by low-temperature heating (low-temperature curing ability), but also high room temperature storage stability. Storage stability refers to a sealant's property of being less reactive at room temperature allowing for stable storage. The efficiency with which a sealant is applied onto a substrate increases with increasing room temperature storage stability. However, due to the presence of hydroxyl groups, which are highly reactive groups, in the molecular structure of the amine imides disclosed by Patent Documents 1 and 2, epoxy resin compositions containing the compound exhibit low storage stability.

Thus, there is a growing need for latent curing agents that may provide epoxy resin compositions exhibiting high low-temperature curing ability and high room temperature storage stability.

In view of the foregoing problems, it is therefore an object of the present invention to provide a latent curing agent which may provide an epoxy resin composition exhibiting high low-temperature curing ability and high room temperature storage stability.

It is another object of the present invention to provide an epoxy resin composition which contains the above latent curing agent and thus exhibits high low-temperature curing ability and high room temperature storage stability; a sealant; and an organic EL display including the sealant.

Means for Solving the Problem

First of all, the inventors established that the N—N bond energy in an amine imide can be reduced to relatively low level by introducing in its molecular structure a substituent that can donate electrons to the N—N bond or by introducing a bulky substituent near the N—N bond. Finally, the inventors established that epoxy resins or the like can be cured even by low-temperature heating when such an amine imide with reduced N—N bond energy is employed as a latent curing agent.

The inventors also established that epoxy resin compositions containing a hydroxyl-free amine imide as a latent curing agent exhibit high room temperature storage stability.

Specifically, a first aspect of the present invention relates to latent curing agents described below.

[1] A latent curing agent for curing ionically polymerizable compounds including:
a hydroxyl-free amine imide,
wherein the hydroxyl-free amine imide has an N—N bond energy of 100 to 210 kJ/mol as determined by the B3LYP density functional method.

[2] The latent curing agent according to [1], wherein the amine imide has an N—N bond energy of 100 to 195 kJ/mol.

[3] The latent curing agent according to [1] or [2], wherein the amine imide has the following general formula (1):

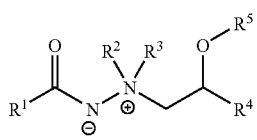

where $R^1$ and $R^4$ each denote an organic group and may be the same or different; $R^2$ and $R^3$ independently denote a non-substituted or substituted alkyl or aryl group or are joined together to form a ring; $R^5$ denotes an organic group; and none of $R^1$ to $R^5$ has an organic group reactive with the ionically polymerizable compounds.

[4] The latent curing agent according to [3], wherein $R^1$ in general formula (1) is a non-substituted or substituted aryl or aryloxy group.

[5] The latent curing agent according to [3] or [4], wherein $R^2$ and $R^3$ in general formula (1) are joined together to form a divalent saturated hydrocarbon having 4 to 8 carbon atoms, a moiety having the formula —$(CH_2)_nO(CH_2)_n$—, or a moiety having the formula —$(CH_2)_nNR^{11}(CH_2)_n$— (where n is a natural number of 2 to 4, and $R^{11}$ is any organic group).

[6] The latent curing agent according to any one of [3] to [5], wherein $R^5$ in general formula (1) is an organic group having a carbonyl group, and the carbon atom of the carbonyl group is bonded to an oxygen atom in general formula (1).

[7] The latent curing agent according to any one of [3] to [6], wherein $R^5$ in general formula (1) is an acyl group.

A second aspect of the present invention relates to epoxy resin compositions, sealant, etc. described below.

[8] An epoxy resin composition including:
(a) the latent curing agent according to any one of [1] to [7]; and
(b) an epoxy resin.

[9] The epoxy resin composition according to [8], further including (c) an acid anhydride.

[10] The epoxy resin composition according to [9], wherein the equivalent ratio of acid anhydride group to epoxy group is 0.8 to 1.2, and the mole ratio of amine imide group to epoxy group is 0.008 to 0.152.

[11] A sealant including the epoxy resin composition according to any one of [8] to [10].

[12] An organic EL display including:
a display substrate having organic EL devices thereon;
a counter substrate which pairs with the display substrate; and
a cured article of the sealant according to [11] between the display substrate and the counter substrate for sealing the organic EL devices.

A third aspect of the present invention relates to amine imides described below.

[13] An amine imide having the following general formula (2):

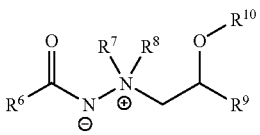

where $R^6$ denotes aryl or aryloxy group which optionally has a substituent other than hydroxyl group; $R^7$ and $R^8$ independently denote an alkyl or aryl group which optionally has a substituent other than hydroxyl group, or are joined together to form a hydroxyl-free ring; $R^9$ denotes an organic group other than hydroxyl group; and $R^{10}$ denotes an alkyl, aryl, aminocarbonyl, acyl or oxycarbonyl group which optionally has a substituent other than hydroxyl group; and none of $R^6$ to $R^{10}$ has groups reactive with epoxy group.

[14] The amine imide according to [13], wherein $R^6$ in general formula (2) is a non-substituted aryl, alkyl-substituted aryl or alkoxy-substituted aryl group.

[15] The amine imide according to [13] or [14], wherein $R^7$ and $R^8$ in general formula (2) are joined together to form a divalent saturated hydrocarbon group having 4 to 8 carbon atoms, a moiety having the formula —$(CH_2)_nO(CH_2)_n$—, or a moiety having the formula —$(CH_2)_nNR^{12}(CH_2)_n$— (where n is a natural number of 2 to 4, and $R^{12}$ is any organic group).

Advantageous Effect of the Invention

The N—N bond in the amine imide contained in a latent curing agent of the present invention is readily cleaved by low-temperature heating to give a tertiary amine that promotes curing of epoxy resins or the like. Thus, epoxy resin compositions containing the latent curing agent exhibit high low-temperature curing ability. Moreover, as the amine imide contains no hydroxyl groups in the molecular structure, the epoxy resin compositions exhibit high room temperature storage stability. Thus, epoxy resin compositions containing a latent curing agent of the present invention exhibit both high low-temperature curing ability and high room temperature storage stability, lending themselves to use as sealants for organic EL displays, for example.

BRIEF DESCRIPTION OF DRAWINGS

FIG. 1 is a table showing results of Examples and Comparative Examples.

BEST MODE FOR CARRYING OUT THE INVENTION

The present invention will be described in detail below. Note in the following description that any numerical range is intended to be inclusive (for example, recitation of "10 to 100" means a numerical range from 10 to 100, inclusive of 10 and 100).

1. Latent Curing Agent

A latent curing agent of the present invention cures ionically polymerizable compounds. The latent curing agent contains a hydroxyl-free amine imide (first amine imide). The hydroxyl-free amine imide has an N—N bond energy of 100 to 210 kJ/mol as determined by the B3LYP density functional method.

The amine imide contained in a latent curing agent of the present invention preferably has the following general formula (1):

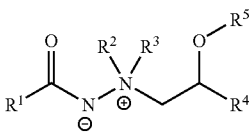

In general formula (1), $R^1$ and $R^4$ each denote an organic group and may be the same or different; $R^2$ and $R^3$ independently denote a non-substituted or substituted alkyl or aryl group or are joined together to form a ring; and R⁵ denotes an organic group. None of $R^1$ to $R^5$ has a hydroxyl group.

The N—N bond energy in an amine imide is a measure of easiness with which the N—N bond in the amine imide is cleaved. Namely, the smaller the N—N bond energy, the more it becomes easy for the N—N bond to be cleaved and therefore the higher the dissociation ability of the amine imide. Thus, amine imides with high dissociation ability exhibit high cure promoting ability for ionically polymerizable compounds.

The N—N bond energy of an amine imide is generally determined by the ab initio method, density functional theory method or the like. It is preferable to employ a density functional theory method because calculations are relatively easy and high-precision calculation results can be obtained. In the present invention, the N—N bond energy of amine imides is determined by "B3LYP," a calculation method known as one of density functional theory methods. As a calculation program, Gaussian 03 Rev. C. 02 can be used. As basis functions, the cc-pVDZ basis set can be used for every element.

More specifically, the following amine imide dissociation reaction represented by Scheme A is assumed. Scheme A shows a dissociation reaction in which an amine imide having general formula (1) is dissociated by cleavage of the N—N bond in its molecular structure to produce an isocyanate having general formula (1-1) and an amine having general formula (1-2).

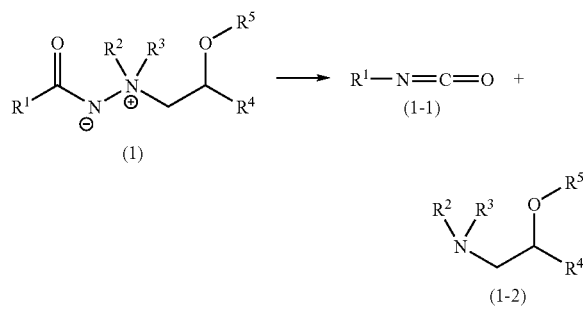

Scheme A $R^1$ to $R^5$ in Scheme A are the same as defined in general formula (1)

The chemical structures of the reactant and products in Scheme A are optimized, followed by calculation of the total energy of each of the compounds. The value of the total energy of the amine imide prior to dissociation is subtracted from the value of the sum of the total energies of the products obtained by dissociation, to find a value of N—N bond energy.

The N—N bond energy of the amine imide as determined by the B3LYP density functional method is preferably 100 to 195 kJ/mol, more preferably 100 to 190 kJ/mol, further preferably 100 to 170 kJ/mol, in order to impart sufficient low-temperature curing ability and storage stability to a resin composition which contains the amine imide as a latent curing agent.

When the N—N bond energy exceeds 210 kJ/mol, the N—N bond becomes so strong that it requires high-temperature heating to effect dissociation of amine imide. On the other hand, when the N—N bond energy is less than 100 kJ/mol, there is concern that the N—N bond is readily cleaved to cause dissociation of the amine imide even at such low temperatures as room temperature to 60° C. Thus, in this case, there is concern that a resin composition which contains such an amine imide exhibits low storage stability.

The N—N bond energy of the amine imide can be adjusted by changing $R^1$ to $R^5$, particularly $R^1$, or $R^2$ and $R^3$, in general formula (1). Substituents $R^1$ to $R^5$ will be described below.

Because amine imides having general formula (1) have potential use as a latent curing agent for curing ionically polymerizable compounds, substituents $R^1$ to $R^5$ are all free from any group which is reactive with ionically polymerizable compounds. More specifically, when the ionically polymerizable compounds are epoxy resins, substituents $R^1$ to $R^5$ do not contain any group which is reactive with epoxy group. Specific examples of the group which is reactive with epoxy group include amino group, phenolic hydroxyl group, thiol group, and carboxyl group. More preferably, substituents $R^1$ to $R^5$ are all free from hydroxyl group for enhanced storage stability as a latent curing agent for epoxy resins. Hydroxyl groups are not necessarily highly reactive with epoxy compounds, but are preferably excluded from amine imides according to the present invention.

$R^1$ in general formula (1) may be any organic group; specific examples thereof include substituted or non-substituted alkyl, aralkyl, alkoxyl, aryl, and aryloxy groups. By employing a highly electron-donating group or a bulky group as substituent $R^1$, the N—N bond energy of the amine imide can be adjusted to fall within the above-specified ranges. Because aryl or aryloxy groups (particularly aryl groups) are also sterically bulky, they may reduce the N—N bond energy in amine imides more significantly than other organic groups.

Examples of alkyl groups for $R^1$ include methyl group, ethyl group, propyl group, butyl group, pentyl group, hexyl group, and heptyl group. These alkyl groups may be either branched or cyclic; cyclic alkyl groups include cyclopentyl group and cyclohexyl group. Examples of aralkyl groups include benzyl group and phenetyl group. Examples of alkoxy groups for $R^1$ include methoxy group, ethoxy group, propoxy group, butoxy group, pentyloxy group, hexyloxy group, and heptyloxy group. The alkoxy groups may be branched or cyclic; cyclic alkoxy groups include cyclopentyloxy group and cyclohexyloxy group.

Examples of aryl groups for $R^1$ include monocyclic, polycyclic or condensed carbocyclic aryl groups such as phenyl group, tolyl group, naphthyl group and anthracenyl group; and heteroaryl groups such as pyridinyl group and quinolyl group. Examples of aryloxy groups for $R^1$ include phenoxy group and naphthoxy group. It should be noted that the alkyl groups, alkoxy groups, aryl groups and aryloxy groups are not specifically limited as long as the effect of the present invention is not impaired.

$R^1$ optionally has substituent(s) other than hydroxyl group. Examples of such optional substituents include alkyl groups, alkoxy groups, aryloxy groups, and acyloxy groups. Among them, alkoxy groups and alkyl groups are preferable in view of enhancing $R^1$'s electron-donating ability.

Examples of alkoxy groups or aryloxy groups to be introduced in $R^1$ include methoxy group, ethoxy group, propoxy group, butoxy group, pentoxy group, phenoxy group, and tolyloxy group. Examples of alkyl groups to be introduced in $R^1$ include methyl group, ethyl group, propyl group, butyl group, pentyl group, hexyl group, heptyl group, octyl group, nonyl group, decyl group, cyclopropyl group, cyclobutyl group, cyclopentyl group, cyclohexyl group, and cycloheptyl group. These substituents may be introduced alone or in combination. When $R_1$ has two or more substituents attached, they may be the same or different.

$R^1$ is preferably an aryl group (particularly phenyl group) in view of its high electron-donating ability and high bulkiness. More preferably, $R^1$ is an aryl group which optionally has an alkyl or alkoxy group as a substituent.

For enhanced $R^1$'s electron-donating ability, phenyl group ($R^1$) may preferably have a substituent attached to the carbon atom at the ortho- or para-position to the carbon atom attached to the carbonyl carbon atom of the amine imide. In particular, substituent $R^1$ becomes more bulky when a substituent is attached to the ortho-carbon atom, and therefore, the N—N bond energy in the amine imide may decrease and thereby dissociation ability increases. When phenyl group ($R^1$) has two substituents attached, preferably, they are respectively attached to the carbon atoms at the ortho- and para-positions to the carbon atom attached to the carbonyl carbon atom of the amine imide.

$R^2$ and $R^3$ in general formula (1) each denote a non-substituted or substituted alkyl or aryl group. It is preferable to make both $R^2$ and $R^3$ bulky in order to reduce the N—N bond energy in the amine imide. Examples of bulky groups include alkyl groups having 1 to 18 carbon atoms and aryl groups having 6 to 18 carbon atoms (e.g., phenyl group), which optionally have a substituent other than hydroxyl group.

$R^2$ and $R^3$ may be joined together to form a ring with a nitrogen atom of the amine imide. This allows $R^2$ and $R^3$ to be formed as a bulky substituent. For example, preferably, $R^2$ and $R^3$ are joined together to form a divalent saturated hydrocarbon having 4 to 8 carbon atoms, a moiety having the formula —$(CH_2)_nO(CH_2)_n$—, or a moiety having the formula —$(CH_2)_nNR^{11}(CH_2)_n$— (where n is a natural number of 2 to 4, and $R^{11}$ is any organic group). $R^{11}$ may be an alkyl group having 1 to 10 carbon atoms, acyl group or sulfonyl group, but is preferably acyl group or sulfonyl group from the viewpoint of storage stability.

For example, when $R^2$ and $R^3$ are joined together to form a moiety having the formula —$(CH_2)_2NR^{11}(CH_2)_2$—, a piperazine ring is formed; when $R^2$ and $R^3$ are joined together to form butylene, a pyrrolidine ring is formed; when $R^2$ and $R^3$ are joined together to form pentylene, a piperidine ring is formed; and when $R^2$ and $R^3$ are joined together to form a moiety having the formula —$(CH_2)_2O(CH_2)_2$—, a morpholine ring is formed.

Alternatively, $R^2$ and $R^3$ may be joined together to form a divalent organic group having formula —$U_n$—$NR^{11}$—$U_n$— (where U is a hydrocarbon having a unsaturated bond). For example, when $U_n$ is a moiety having the formula —CH=CH—, a dihydropyrazine ring is formed.

$R^4$ in general formula (1) is any organic group having no hydroxyl group. Preferably, $R^4$ is a non-substituted or substituted alkyl, aryl or aryloxy group.

Examples of alkyl groups for $R^4$ include methyl group, ethyl group, propyl group, butyl group, pentyl group, hexyl group, heptyl group, octyl group, nonyl group, decyl group, cyclopropyl group, cyclobutyl group, cyclopentyl group, cyclohexyl group, cycloheptyl group, benzyl group, and phenethyl group.

Examples of aryl groups for $R^4$ include monocyclic aryl groups such as phenyl group and tolyl group; condensed cyclic aryl groups such as naphthyl group and anthracenyl group; polycyclic aryl groups such as biphenyl group; and heteroaryl groups such as pyridine group and quinolyl group. Examples of aryloxy groups for $R^4$ include phenoxy group and naphthoxy group.

$R^4$ optionally has a substituent other than hydroxyl group. Examples of such a substituent to be introduced in $R^4$ include alkyl group, alkoxy group, aryloxy group, and acyloxy group. These substituents are identical to those to be introduced in $R^1$.

$R^5$ in amine imides having general formula (1) enhances resin composition's room temperature storage stability as it functions as a "capping group" that prevents the amine imide from reacting with other components (mainly acid anhydride) in the resin composition.

Any hydroxyl-free organic group suffices as substituent $R^5$ in general formula (1). Preferably, $R^5$ is an alkyl group, aryl group, carbonyl-containing organic group, or sulfonyl-containing organic group, which optionally have a substituent other than hydroxyl group.

Examples of alkyl groups for $R^5$ include methyl group, ethyl group, propyl group, butyl group, benzyl group, and phenethyl group. Examples of aryl groups for $R^5$ include monocyclic aryl groups such as phenyl group and tolyl group; condensed cyclic aryl groups such as naphthyl group and anthracenyl group; polycyclic aryl groups such as biphenyl group; and heteroaryl groups such as pyridine group and quinolyl group.

Examples of carbonyl-containing organic groups for $R^5$ include N-substituted aminocarbonyl groups such as N-alkyl-aminocarbonyl groups and N-aryl-aminocarbonyl groups; formyl group; acyl groups such as acetyl group, isopropylcarbonyl group, butylcarbonyl group, and benzoyl group; and O-substituted oxycarbonyl groups such as methyloxycarbonyl group, benzyloxycarbonyl group, and t-butoxycarbonyl group.

Examples of substituents to be introduced to $R^5$ include alkyl group, alkoxy group, aryloxy group, and acyloxy group. Specific examples of these substituents are identical to those to be introduced in $R^1$.

Specific examples of amine imides having general formula (1) include, but not limited to, compounds shown below.

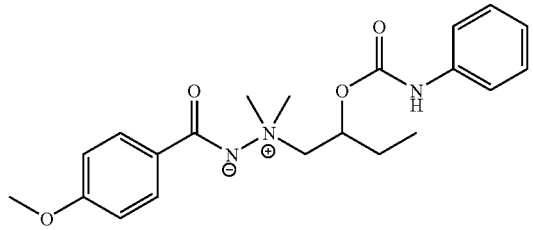

(3)

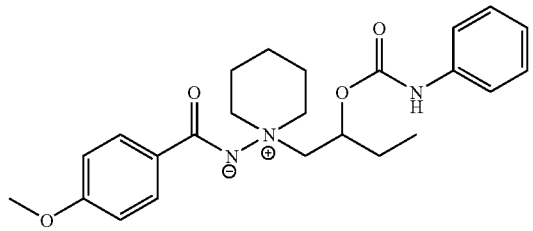

(4)

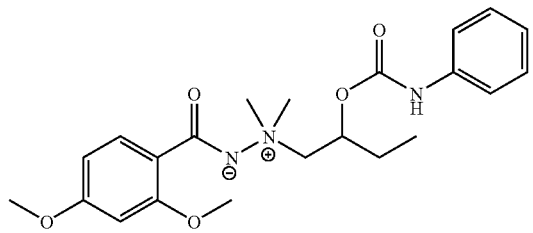

(5)

(6)
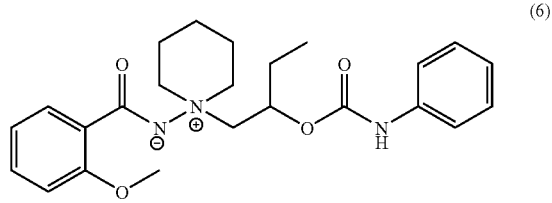

(7)
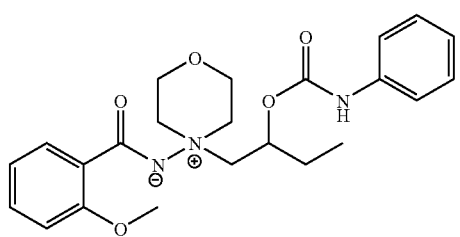

(8)
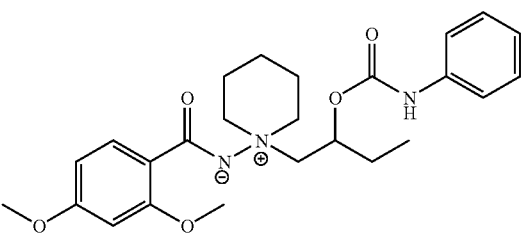

(9)
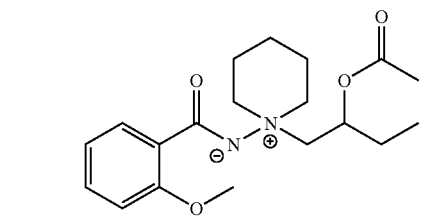

(10)
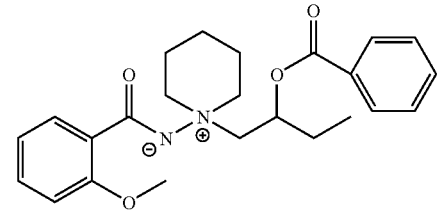

(11)
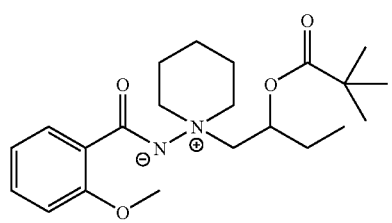

(12)
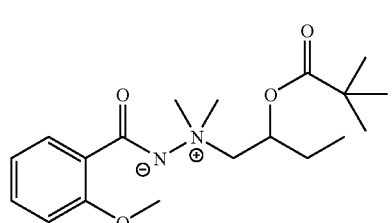

(13)
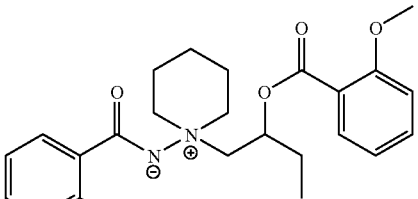

(14)
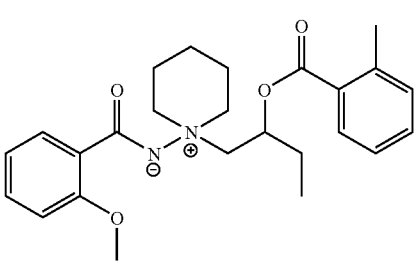

At room temperature, amine imides used in the present invention includes a latent (i.e., inactive) tertiary amine. Because the amine imides are low in their N—N bond energy, they undergo dissociation by low-temperature heating to produce an isocyanate and a tertiary amine. The produced tertiary amine acts as a curing promoter that promotes curing or polymerization of ionically polymerizable compounds such as epoxy resins. Accordingly, latent curing agents which contain the amine imide can produce epoxy resin compositions with high low-temperature curing ability.

Latent curing agents need to be non-reactive with ionically polymerizable compounds under normal conditions (e.g., at room temperature). Amine imides are non-reactive with ionically polymerizable compounds as they never produce amines until the N—N bond in their molecular structure is cleaved. However, the inventors found that some amine imides, even when the N—N bond is not cleaved, cause undesirable promotion of curing or polymerization of ionically polymerizable compounds. The inventors identified the cause of the promotion of curing or polymerization as the presence of a hydroxyl group in the amine imide. Moreover, by capping the hydroxyl group, the inventors succeeded in obtaining latent curing agents having high storage stability. It is thus made possible to provide epoxy resin compositions with high storage stability, which can stably remain uncured at room temperature while exhibiting high low-temperature curing ability.

2. Preparation Method of Amine Imides

Amine imides used in a latent curing agent of the present invention can be prepared with any method, as long as the effect of the present invention is not impaired. The following describes a preferable preparation method of amine imides.

For example, an amine imide can be prepared according to Scheme 1-1 or Scheme 1-2 shown below. The schemes illustrate reaction between an amine imide having a hydroxyl group in its molecular structure which has general formula (15) (hereinafter also referred to as "hydroxyl-containing amine imide (a)") and a compound reactive with a hydroxyl group, which has general formula (16) or (16') (hereinafter also referred to as "capping agent (b)").

Scheme 1-1

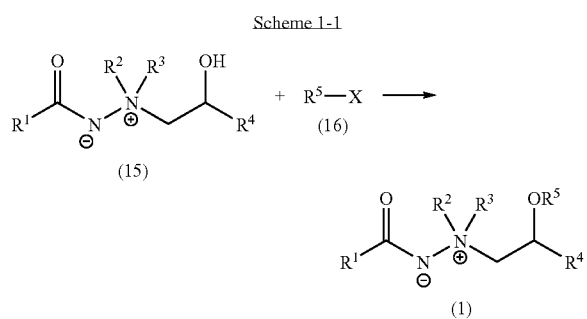

Scheme 1-2

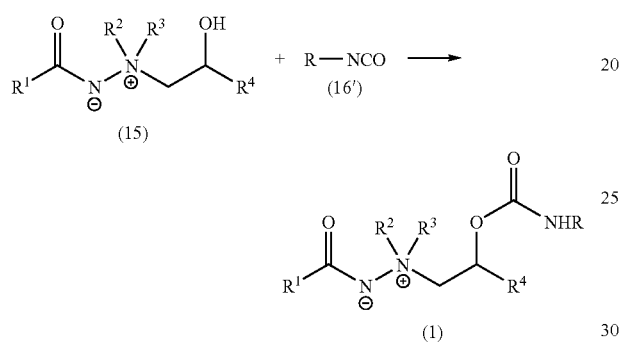

R$^1$ to R$^5$ in Schemes 1-1 and 1-2 are the same as defined in general formula (1). A compound having general formula (16) or (16') reacts with a hydroxyl group of a compound having general formula (13). From the compound having general formula (16), substituent X is eliminated by reaction with the hydroxyl group, and then R$^5$ bonds to the oxygen atom of the hydroxyl group. On the other hand, an isocyanate having general formula (16') reacts with the hydroxyl group to form a urethane bond. The reactions in Schemes 1-1 and 1-2 can be effected as follows: Hydroxyl-containing amine imide (a) is dissolved or dispersed in suitable solvent in a reaction vessel; as capping agent (b) a compound having general formula (16) or (16') is added to the reaction vessel; and the mixture is stirred with or without heating. Additive(s) may be added to the reaction vessel as a reaction promoter. When the compound having general formula (16) is, for example, an acid halide, it may be added dropwise on ice in the presence of a base as an additive, and the mixture is stirred with or without heating.

R$^1$ to R$^4$ in amine imides having general formula (1) are groups derived from hydroxyl-containing amine imide (a), and R$^5$ is a group derived from capping agent (b). Thus, the molecular structure of the amine imide having general formula (1) is adjusted by appropriate molecular designing of hydroxyl-containing amine imide (a) and capping agent (b).

Source compounds for amine imides having general formula (1) will be described below.

[Hydroxyl-Containing Amine Imide (a)]

Hydroxyl-containing amine imide (a) may be prepared in accordance with a known synthesis procedure. For simplicity and safety of synthesis reaction, it is preferably prepared by reaction of three components—carboxylic acid derivative (A), hydrazine derivative (B), and epoxy compound (C). Specifically, an equimolar mixture of carboxylic acid derivative (A), hydrazine derivative (B) and epoxy compound (C) may be mixed in a solvent. In this reaction, reaction temperature may be appropriately set.

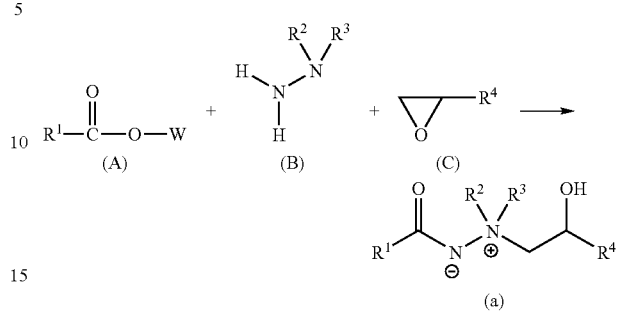

Carboxylic acid derivative (A) is, for example, a compound having general formula (A1) or (A2).

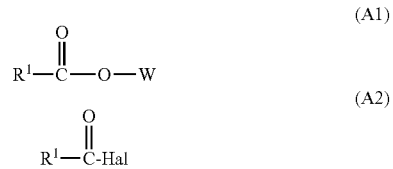

In general formula (A1), R$^1$ is the same as defined in general formula (1), and W denotes any organic group.

In general formula (A2), R$^1$ is the same as defined in general formula (1), and Hal denotes a halogen atom.

Carboxylic acid derivative (A1) may be either a carboxylic acid or carboxylic acid ester. Examples of carboxylic acids or carboxylic acid esters include alkyl-substituted benzoic acids such as 3-methylbenzoic acid, 4-methylbenzoic acid, 3,5-dimethylbenzoic acid, and 2,4,6-trimethylbenzoic acid; alkoxy-substituted benzoic acids such as 2-methoxybenzoic acid, 3-methoxybenzoic acid, 4-methoxybenzoic acid, 2-methoxy-6-methylbenzoic acid, 2,4-dimethoxybenzoic acid, 3,4-dimethoxybenzoic acid, 3,5-dimethoxybenzoic acid, 3,4,5-trimethoxybenzoic acid, and 4-ethoxybenzoic acid; and C1-C4 alkyl esters thereof.

Carboxylic acid derivative (A2) is an acid halide in which the hydroxyl group of a carboxylic acid is replaced by a halogen atom. Examples of acid halides include carboxylic chlorides and carboxylic bromides.

R$^1$ in amine imides having general formula (1) is determined by appropriate molecular designing of carboxylic acid derivative (A). Among other groups for R$^1$, phenyl group having a substituent at the ortho position is more preferable as it enhances dissociation ability of the amine imides.

Hydrazine derivative (B) is, for example, a compound having general formula (B) below. R$^2$ and R$^3$ in the amine imide having general formula (1) are determined by appropriate molecular designing of the hydrazine derivative.

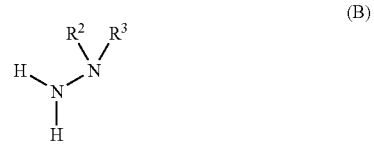

where R$^2$ and R$^3$ are the same as defined in general formula (1).

Examples of hydrazine derivative (B) include, but not limited to, dimethylhydrazine, diethylhydrazine, methyl ethyl hydrazine, methyl propyl hydrazine, methyl butyl hydrazine, methyl pentyl hydrazine, methyl hexyl hydrazine, ethyl propyl hydrazine, ethyl butyl hydrazine, ethyl pentyl hydrazine, ethyl hexyl hydrazine, dipropylhydrazine, dibutylhydrazine, dipentylhydrazine, dihexylhydrazine, methyl phenyl hydrazine, ethyl phenyl hydrazine, methyl tolyl hydrazine, ethyl tolyl hydrazine, diphenylhydrazine, benzyl phenyl hydrazine, dibenzylhydrazine, dinitrophenylhydrazine, N-aminopiperidine, N-aminohomopiperidine, N-amino-2,6-dimethylpiperidine, N-aminopyrrolidine, N-amino-2-methylpyrrolidine, N-amino-2-phenylpyrrolidine, N-aminopyrrole, N-amino-2,5-dimethylpyrrole, N-aminopyrroline, N-amino-2-phenylpyrroline, and N-aminomorpholine.

Among them, dimethylhydrazine, N-aminopiperidine, and N-aminomorpholine are more preferable because amine imides can be prepared at low temperatures and the N—N bond can be readily maintained.

Epoxy compound (C) is a compound having an epoxy group in its molecule and has, for example, general formula (C) below. $R^4$ in the amine imide having general formula (1) is determined by appropriate molecular designing of epoxy compounds (C).

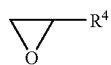   (C)

where $R^4$ is the same as defined in general formula (1).

Examples of epoxy compound (C) include ethylene oxide, propylene oxide, cyclohexene oxide, 1-octane oxide, n-butyl glycidyl ether, allyl glycidyl ether, and phenyl glycidyl ether.

Upon preparation of hydroxyl-containing amine imide (a), a solvent may be used. Examples of suitable solvents include, but not limited to, alcohols such as methanol, ethanol, propanol, isopropanol, and butanol; and ethers such as tetrahydrofuran and diethylether. A suitable solvent is appropriately selected in view of, for example, its compatibility with the source compounds of hydroxyl-containing amine imide (a)—carboxylic acid derivative (A), hydrazine derivative (B), and epoxy compound (C).

Examples of hydroxyl-containing amine imide (a) include, but not limited to, compounds shown below.

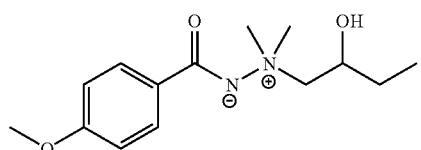   (17)

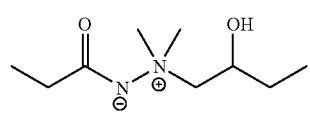   (18)

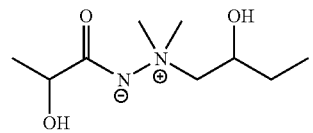   (19)

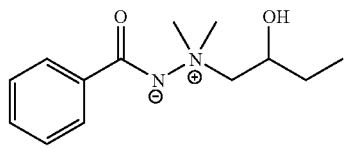   (20)

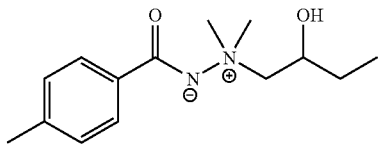   (21)

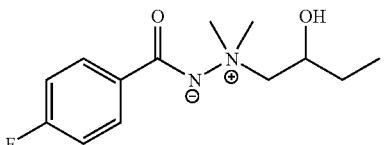   (22)

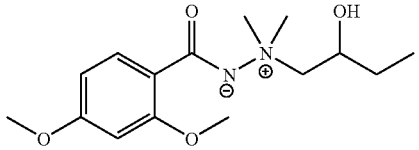   (23)

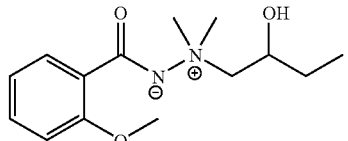   (24)

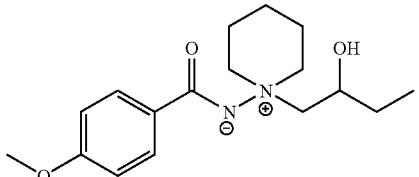   (25)

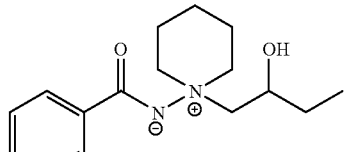   (26)

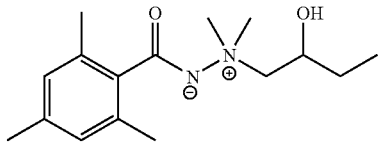   (27)

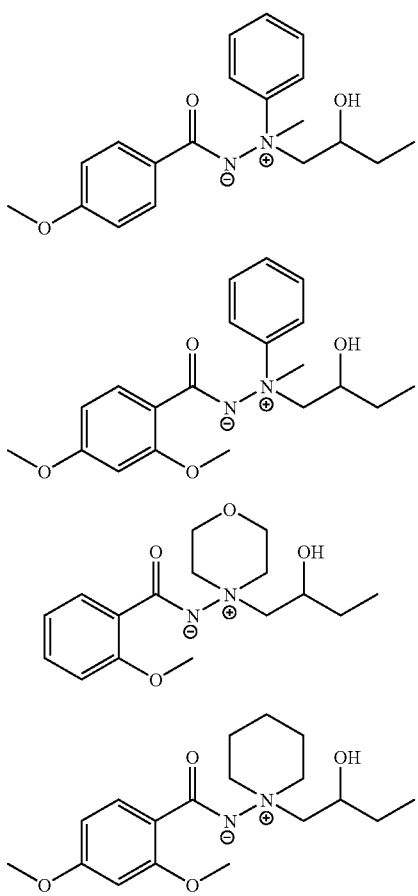

[Capping Agent (b)]

Capping agent (b) is a compound having general formula (16) in Scheme 1-1 or general formula (16') in Scheme 1-2. Compounds having general formula (16) generally have X group, a leaving group, and an organic group (capping group for hydroxyl group) which corresponds to $R^5$ in the amine imide having general formula (1). Compounds having general formula (16) are, for example, carboxylic compounds where $R^5$ is an acyl or oxycarbonyl group. Compounds having general formula (16') have an isocyanate group which forms a urethane bond by reaction with a hydroxyl group, capping the hydroxyl group. $R^5$ in the amine imide having general formula (1) is determined by appropriate molecular designing of capping agent (b).

Examples of carboxylic compounds having general formula (16) include aliphatic carboxylic acids such as formic acid, acetic acid, propionic acid, butyric acid, valeric acid, pivalic acid, oleic acid, linoleic acid, oxalic acid, and succinic acid; aromatic carboxylic acids such as benzoic acid, phthalic acid, and terephthalic acid; other carboxylic compounds like pyruvic acid, lactic acid, fumaric acid, and maleic acid; and derivatives thereof. Examples of derivatives of carboxylic compounds include acid anhydrides, esters and acid halides thereof.

Examples of isocyanates having general formula (16') include aromatic isocyanates such as phenyl isocyanate, tolyl isocyanate, ethyl phenyl isocyanate, p-isopropylphenyl isocyanate, 2,6-dimethylphenyl isocyanate, mesityl isocyanate, methoxyphenyl isocyanate, 3,5-dimethoxyphenyl isocyanate, acetyl phenyl isocyanate, p-dimethylaminophenyl isocyanate, p-toluene sulfonyl isocyanate, p-trifluoromethylphenyl isocyanate, pentafluorophenyl isocyanate, p-chlorophenyl isocyanate, nitrophenyl isocyanate, benzyl isocyanate, benzoyl isocyanate, 2-biphenyl isocyanate, diphenylmethyl isocyanate, 2-phenoxyphenyl isocyanate, 1-napthyl isocyanate, 1-adamantyl isocyanate, fluorenyl isocyanate, triphenylmethyl isocyanate, and thienyl isocyanate; aliphatic isocyanates such as methyl isocyanate, ethyl isocyanate, propyl isocyanate, butyl isocyanate, hexyl isocyanate, and ethoxycarbonyl isocyanate; and alicyclic isocyanates such as cyclopentyl isocyanate and cyclohexyl isocyanate.

For enhanced reactivity with hydroxyl group, capping agent (b) is preferably an acid anhydride or acid halide having general formula (16) or isocyanate having general formula (16'). Hydroxyl-containing amine imide (a) is prone to dissociation due to low N—N bond energy in the molecular structure. The acid anhydrides, acid halides and isocyanates are highly reactive with a hydroxyl group and thus react it even without heating, capping the hydroxyl group without causing dissociation of unstable hydroxyl-containing amine imide (a) to yield an amine imide having general formula (1).

In order to fully cap hydroxyl groups of hydroxyl-containing amine imide (a) during capping reaction, hydroxyl-containing amine imide (a) and capping agent (b) are preferably formulated in amounts so that the equivalent ratio of total hydroxyl groups to total capping groups ranges from 1 to 5. When the total hydroxyl groups-to-total capping groups equivalent ratio exceeds 5, it may become difficult to isolate the resultant amine imide. On the other hand, when the equivalent ratio is less than 1, only some of the hydroxyl groups of hydroxyl-containing amine imide (a) molecules would be capped.

A solvent may be used in the capping reaction; examples thereof include, but not limited to, alcohols, ethers and acetic esters, and halogen-based solvents such as chloroform and dichloromethane. The solvent may be selected in view of, for example, its compatibility with the source compounds.

For capping of the hydroxyl group of hydroxyl-containing amine imide (a) using an isocyanate as capping agent (b), for example, a mixture of isocyanate, hydroxyl-containing amine imide (a) and solvent may be stirred for 0.1 to 24 hours at room temperature to 100° C. in the presence of a small amount of base. When a carboxylic compound (e.g., carboxylic anhydride or acid halide) is used as capping agent (b) for capping the hydroxyl group of hydroxyl-containing amine imide (a), for example, a mixture of an acid anhydride or acid halide, hydroxyl-containing amine imide (a) and solvent may be stirred for 0.1 to 24 hours at room temperature to 100° C. in the presence of a reaction promoter such as a base.

The progress of capping reaction can be monitored by thin layer chromatography (TLC), high-performance liquid chromatography (HPLC), or measuring changes over time in hydroxyl group equivalent in the reaction solution. The measurement method of hydroxyl equivalent is not specifically limited; for example, a portion of the reaction solution is sampled at given time intervals for the measurement of the hydroxyl value with a hydroxyl value meter or by a known titration method.

3. Resin Composition

A resin composition according to the present invention contains at least a latent curing agent of the present invention and an ionically polymerizable compound. Any ionically polymerizable compound suffices as long as it polymerizes or cures by the latent curing agent. For example, epoxy resins, polyamide resins, polyamideimide resins polyurethane resins, vinyl-containing compounds (e.g., acrylic resins), and thioether compounds (e.g., episulfides and thietanes) can be used. Among them, epoxy resins are preferable.

The following describes an example where epoxy resins are used as ionically polymerizable compounds. There is no particular limitation to epoxy resins as long as they contain epoxy group in the molecule. Among other types of epoxy resins, liquid epoxy resins provide homogeneous epoxy resin compositions as they are more compatible to other resin composition's components at room temperature. Examples of such liquid epoxy resins include, but not limited to, bisphenol A epoxy resins and bisphenol F epoxy resins.

Epoxy resin compositions may further contain an acid anhydride, a compound in which two carboxyl groups are condensed by dehydration. Carboxyl groups generated by cleavage of an acid anhydride are highly reactive with epoxy groups. Thus, acid anhydrides are not only suitable for use as curing agents for epoxy resins, but also can provide transparent resin compositions. The reaction between epoxy resin and acid anhydride is promoted by a tertiary amine generated from the amine imide of a latent curing agent of the present invention.

Examples of acid anhydrides include, but not limited to, methylhexahydrophthalic anhydride, hexahydrophthalic anhydride, methyltetrahydrophthalic anhydride, tetrahydrophthalic anhydride, methyl nadic anhydride, acetic anhydride, propionic anhydride, benzoic anhydride, succinic anhydride, maleic anhydride, and phthalic anhydride. Other known acid anhydrides can also be used.

It is more preferable to employ methylhexahydrophthalic anhydride for the purpose of obtaining epoxy resin compositions with high transparency and high curing ability. Alternatively, as the acid anhydride, it is also possible to use a multifunctional acid anhydride like 4-(2,5-dioxotetrahydrofuran-3-yl)-1,2,3,4-tetrahydronaphthalene-1,2-dicarboxylic anhydride or 5-(2,5-dioxotetrahydro-3-cyclohexene)-1,2-dicarboxylic anhydride. Using acid anhydrides that are liquid at room temperature, homogeneous epoxy resin compositions can be produced.

In order to for a latent curing agent which contains an amine imide to fully exert its cure promotion effect as a curing promoter for polymerization or curing of epoxy resin, the mole ratio of amine imide group to epoxy group in the epoxy resin composition is preferably 0.008 to 0.152, more preferably 0.010 to 0.100, most preferably 0.015 to 0.075.

When the amine imide group-to-epoxy group mole ratio exceeds 0.152, it results in non-reacted amine imide molecules abundantly remaining in the cured epoxy resin composition, which may adversely affect physical properties of the cured material. On the other hand, when the amine imide group-to-epoxy group mole ratio is less than 0.008, it may result in failure to fully cure epoxy resin.

An epoxy resin composition containing epoxy resin and acid anhydride is cured in such a way that epoxy groups and acid anhydride groups are alternately linked together. Thus, epoxy resin and acid anhydride are added in substantially equivalent amounts. In the present invention, the equivalent ratio of acid anhydride group to epoxy group in the epoxy resin composition is preferably 0.8 to 1.2.

When the acid anhydride group-to-epoxy group equivalent ratio is greater than 1.2 or less than 0.8, the acid anhydride or epoxy resin, whichever is more dominant, remains unreacted in the cured material and may adversely affect physical properties of the cured material The epoxy resin compositions may further contain an coupling agent for the purpose of improving interface adhesion between the epoxy resin composition and a substrate to which it is applied. Examples of coupling agents include, but not limited to, silane coupling agents and titanium coupling agents.

The coupling agent may be a compound in which some or all of the hydrogen atoms participating in the carbon-hydrogen bonds are replaced by fluorine atoms. The coupling agent content is preferably 0 to 30 parts by weight per 100 parts by weight of epoxy resin.

For improved heat resistance, water resistance, etc., the epoxy resin compositions may contain various additives as needed, including fillers such as organic or inorganic fillers; modifiers such as antiaging agents and plasticizers; and stabilizers such as ultraviolet absorbers, antiseptic agents, and antibacterial agents.

[Filler]

There is no particular limitation to fillers used in the present invention; organic or inorganic fillers may be used. Inorganic fillers are inorganic fine particles with a primary particle diameter of 0.005 to 10 μm.

Examples of inorganic fillers include, but not limited to, silica, talc, alumina, mica, and calcium carbonate. Inorganic fillers may or may not be surface treated by methoxylation, trimethylsilylation, octylsilylation, or treated with silicone oils.

Organic fillers are particles made of organic matter. Examples of organic fillers include, but not limited to, styrene polymer particles, methacrylate polymer particles, ethylene polymer particles, and propylene polymer particles. Regardless of the type of the material, these fillers may be used alone or in combination.

The filler content is preferably 0 to 500 parts by weight per 100 parts by weight of epoxy resin. When the filler content falls within this range, epoxy resin compositions can be obtained having high moisture permeation resistance, high adhesion, etc. The filler content may be appropriately adjusted depending on the required transparency, viscosity, etc., of a sealant to be manufactured.

[Modifier]

Modifiers are components that alter the inherent property of resin compositions. Examples of modifiers include polymerization initiators, antiaging agents, leveling agents, wettability improvers, surfactants, plasticizers, and flexibilizers. These agents may be used alone or in combination.

[Additional Resin]

The epoxy resin compositions may further contain additional resins other than epoxy resin. Examples thereof include polyamides, polyamideimides, polyurethanes, polybutadienes, polychloroprenes, polyethers, polyesters, styrene-butadiene-styrene block copolymers, petroleum resins, xylene resins, ketone resins, cellulose resins, fluorine oligomers, silicon oligomers, and polysulfide oligomers. These additional resins may be used alone or in combination.

The epoxy resin compositions may also contain a thiol compound and/or phenol compound. Thiol compounds have a thiol group in the molecular structure. There is no particular limitation to thiol compounds; known thiol compounds may also be used. Phenol compounds are compounds having a phenol group in the molecular structure. Specific examples thereof include, but not limited to, phenol, methyl phenol, ethyl phenol, and isopropyl phenol.

A latent curing agent of the present invention may be used together with crosslinkable resins other than epoxy resin. In this case, the latent curing agent acts as a curing agent or curing promoter for the crosslinkable resins.

Examples of crosslinkable resins include compounds having unsaturated bonds that allow for the Michael addition reaction, and compounds having alkoxysilyl groups exhibiting sol-gel reaction.

Examples of crosslinkable resin compositions are, for example, crosslinkable resin compositions which contain a latent curing agent of the present invention, an isocyanate which forms urethane resin, and a polyol. The crosslinkable resin composition may further contain an acid anhydride, thiol compound, or phenolic compound.

[Storage Stability of Resin Composition]

The storage stability of the epoxy resin composition is described by a change in its viscosity before and after a 24-hour storage at room temperature, i.e., viscosity ratio expressed as "viscosity after storage (mPa·s)/viscosity before storage (mPa·s)." The viscosity ratio is preferably 1.0 to less than 2.0, more preferably 1.0 to less than 1.5. When the viscosity ratio is 1.0, it means that there was no change in viscosity before and after storage of the epoxy resin composition. Thus, the viscosity ratio is preferably as close as 1.0, because the epoxy resin compositions are much less likely to undergo viscosity changes.

The viscosity of the epoxy resin composition may be measured with an E-type viscometer. Measurement temperature may be set to 25° C., and measurement time may be set to 3 minutes.

[Low-Temperature Curing Ability of Resin Composition]

Low-temperature curing ability of the epoxy resin composition may be evaluated by differential scanning calorimetry (DSC). Specifically, a sample is prepared in which an epoxy resin composition is sandwiched between two 5 mm-thick NaCl crystal plates. The sample is measured for its infrared transmission spectra with a known FT-IR spectrometer, before and after heat treatment at given temperature for a given period of time. In each IR spectrum the height of an absorption peak caused by asymmetric stretching vibrations of the epoxy group (near 910 $cm^{-1}$) is divided by the height of an absorption peak caused by in-plane C—C stretching vibrations of the benzene ring (near 1,600 $cm^{-1}$) to standardize the absorption peak derived from the epoxy group. The reaction ratio of epoxy groups was then calculated based on the attenuation level of the epoxy group-derived absorption peak due to heat treatment.

4. Sealant Containing a Resin Composition, and an Organic EL Display Manufactured Using the Sealant.

An epoxy resin composition containing a latent curing agent of the present invention is suitable as a one-component resin composition, which is composed of a homogeneous mixture of a cure promoting component (e.g., amine imide), a curable component (e.g., epoxy resin) and a curing component (e.g., acid anhydride), and remains unchanged during room temperature storage as the curing component and curable component remain unreacted at that temperature.

Such a one-component resin composition is more easy to handle and less bothersome than a two-component counterpart that requires mixing of a curing component and a curable component prior to use, as there is no need to perform weighing, mixing, and stirring of these components.

Moreover, uniform resin curing can be achieved in the resin composition containing a latent curing agent of the present invention, because components associated with curing reaction are homogeneously mixed together. This reduces the likelihood of local generation of physical property unevenness after curing, allowing the cured material to be used as a high-reliability material. Also, the resin composition is suitable in applications where high transparency is required after curing.

At room temperature the epoxy resin composition does not cure and is stable in viscosity, but cures by low-temperature heating. This property makes the epoxy resin composition applicable to such industrial materials as paints, adhesives, photoresists, automotive parts, electric/electro materials, and optical materials. The epoxy resin composition is particularly useful as an adhesive or coating agent for low-heat resistance members and as a sealant for liquid crystal or organic EL devices, which are susceptible to degradation by heat.

The epoxy resin composition is also useful as an adhesive for opaque members like metals, as it fully cures at low temperatures without exposure to light such as ultraviolet light. Because full curing is achieved only by heating, the epoxy resin composition can also be used for sealing of organic EL devices which degrade by irradiation with ultraviolet light.

The following describes an example where an epoxy resin composition containing a latent curing agent of the present invention is applied as a sealant for an organic EL display.

An organic EL display includes a display substrate having organic EL devices thereon, and a counter substrate which pairs with the display substrate. A sealant for sealing the organic EL devices is applied between the display substrate and counter substrate.

Sealants for organic EL displays are used as agents for sealing liquid crystals or organic EL devices or as adhesives for display substrates of various image display devices.

A sealant of the present invention contains a latent curing agent of the present invention and epoxy resin, and therefore exhibits high room temperature storage stability and high low-temperature curing ability. Further, it exhibits high transparency when an acid anhydride is combined. Thus, the sealant is particularly suitable for manufacture of a so-called "cover-sealing organic EL display" in which all organic EL devices are covered with a sealant.

Cover-sealing organic EL displays can offer higher display strength than organic EL displays in which organic EL devices are sealed using a frame, and their organic EL devices can be directly sealed with a sealant. This eliminates the need for the use of a mask which has been used for the protection of organic EL devices, leading to the expectation of simplification of the manufacturing process and reduced manufacturing costs.

There is no particular limitation to the method of applying a sealant on the substrate of an organic EL display; any coating method can be used which can uniformly apply a sealant on the substrate. Examples of known coating methods include screen printing and dispensing. Alternatively, a sealant may be loaded between a display substrate and a sealing substrate, which is a plate member with excellent moisture-proof property, such as a resin film, glass plate or metal plate.

The sealant viscosity can be adjusted by changing the ratios of resin and/or other additives in the sealant. The sealant viscosity is preferably 100 to 10,000 mPa·s, more preferably 500 to 8,000 mPa·s, and may be measured with an E-type viscometer (RC-500, Toki Sangyo Co., Ltd.) at 25° C. Preferably, the sealant is so prepared that respective components are homogeneously mixed therein, from the viewpoint of handling suitable for "cover-sealing organic EL display".

5. Second Amine Imides

Second amine imides according to the present invention have the following general formula (2):

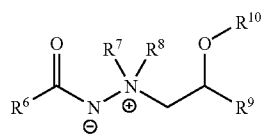

(2)

In general formula (2), $R^6$ denotes an aryl or aryloxy group which optionally has a substituent other than hydroxyl group; $R^7$ and $R^8$ independently denote an alkyl or aryl group which optionally has a substituent other than hydroxyl group or are joined together to form a hydroxyl-free ring; $R^9$ denotes an organic group other than hydroxyl group; and $R^{10}$ denotes an alkyl, aryl, aminocarbonyl, acyl or oxycarbonyl group which optionally has a substituent other than hydroxyl group. None of $R^6$ to $R^{10}$ has groups reactive with epoxy group.

$R^6$ in general formula (2) denote the same aryl group or aryloxy group which optionally has a substituent other than hydroxyl group as defined for $R^1$ of general formula (1). Preferably, $R^6$ is a non-substituted, alkyl-substituted, or alkoxy-substituted aryl group.

$R^7$ and $R^8$ in general formula (2) each denote the same optionally substituted alkyl or aryl group as defined for $R^2$ and $R^3$ in general formula (1) or are joined together to form a hydroxyl-free ring in the same way that $R^2$ and $R^3$ in general formula (1) are joined together. $R^7$ and $R^8$ in general formula (2) are preferably joined together to form a saturated hydrocarbon group having 4 to 8 carbon atoms, a moiety having the formula —$(CH_2)_n$—$(CH_2)_n$—, or a moiety having the formula —$(CH_2)_n NR^{12}(CH_2)_n$— (where n is a natural number of 2 to 4, and $R^{12}$ is any organic group). $R^{12}$ may be, for example, an alkyl group having 1 to 10 carbon atoms, acyl group or sulfonyl group, but is preferably acyl group or sulfonyl group from the viewpoint of storage stability.

$R^9$ in general formula (2) denotes the same organic group other than hydroxyl group as defined for $R^4$ in general formula (1).

$R^{10}$ in general formula (2) denotes the same alkyl, aryl, aminocarbonyl, acyl or oxycarbonyl group which optionally has a substituent other than hydroxyl group, as defined for $R^5$ in general formula (1).

Due to the unstable N—N bond in their molecular structure and steric hindrance, the second amine imides readily undergo dissociation even by low-temperature heating to produce an isocyanate and a tertiary amine. Meanwhile, in the second amine imide, the hydroxyl group is capped with a capping agent.

Thus, an epoxy resin composition which contains the second amine imide, acid anhydride and epoxy resin can suppress viscosity increase because the amine imide does not react with epoxy groups at room temperature. Moreover, even by low-temperature heating, it yields a tertiary amine that promotes curing reaction between the epoxy resin and acid anhydride. When the second amine imide is dissociated, it produces an isocyanate in addition to a tertiary amine. The isocyanate thus produced reacts with hydroxyl or other groups generated by the ring-opening of the epoxy group. Thus, the isocyanate never adversely affects the cured epoxy resin composition.

EXAMPLES

The present invention will be described in detail with reference to Examples and Comparative Examples, which however shall not be construed as limiting the scope of the invention thereto.

[Preparation of Hydroxyl-Containing Amine Imide A]

16.62 g (0.10 mol) of methyl 4-methoxybenzoate, 6.01 g (0.10 mol) of N,N-dimethylhydrazine, and 7.21 g (0.10 mol) of 1,2-epoxybutane were dissolved in 80 mL of t-butanol. The solution was reacted under stirring at 55° C. for 40 hours. After the reaction was completed, the solution was condensed in vacuo to remove the solvent and by-product methanol to give a viscous condensate. The viscous condensate was dissolved in 2 volumes of ethyl acetate. The solution was purified on a column packed with NH-silica gel (Fuji Silysia Chemical Ltd.) eluting with methanol/ethyl acetate (1:10). The purified product was crystallized using hexane and dried in vacuo to give 13.1 g of white crystals with 99.6% purity (yield: 49.0 mol %).

A part of the white crystals was sampled and $^1$H-NMR characterization was carried out on JEOL EXcalibur270 spectrometer (25° C., CDCl$_3$, 270 MHz) to identify the crystal structure:

7.80 (d, 2H, C$_6$H$_4$), 6.83 (d, 2H, C$_6$H$_4$), 4.23-4.08 (m, 1H, CHOH), 3.80 (s, 3H$_2$OCH$_3$), 3.64 (d, 6H, NCH$_3$), 3.56-3.10 (m, 2H, NCH$_2$), 1.65-1.44 (m, 2H, CH$_2$CH$_3$), 1.03 (t, 3H, CH$_2$CH$_3$)

A part of the white crystals was sampled and mass spectrometric analysis was carried out using ESI-MS (ZND, Micromass Inc.). The measured value was 267.2. These results confirm that the obtained white crystals were hydroxyl-containing amine imide A, i.e., 1,1-dimethyl-1-(2-hydroxybutyl)amine p-methoxybenzimide.

[Preparation of Hydroxyl-Containing Amine Imide B]

16.62 g (0.10 mol) of methyl 2-methoxybenzoate, 10.52 g (0.105 mol) of 1-aminopiperidine, and 7.57 g (0.105 mol) of 1,2-epoxybutane were dissolved in 100 mL of t-butanol. The solution was reacted under stirring at 60° C. for 3 days. After the reaction was completed, the solution was condensed in vacuo to remove the solvent and by-product methanol to give a viscous condensate. The viscous condensate was dissolved in 2 volumes of ethyl acetate. The solution was purified on a column packed with NH-silica gel (Fuji Silysia Chemical Ltd.) eluting with methanol/ethyl acetate (1:10). The purified product was crystallized using hexane and dried in vacuo to give 14.88 g of white crystals with 96.4% purity (yield: 46.8 mol %).

A part of the white crystals was sampled and $^1$H-NMR characterization was carried out on JEOL EXcalibur270 spectrometer (25° C., CDCl$_3$, 270 MHz) to identify the crystal structure:

7.42 (d, 1H, C$_6$H$_4$), 7.31-7.17 (m, 1H, C$_6$H$_4$), 6.97-6.80 (m, 2H, C$_6$H$_4$), 4.89-4.71 (m, 2H, C$_5$H$_{10}$), 4.62-4.51 (m, 2H, C$_5$H$_{10}$), 4.33-4.20 (m, 1H, CHOH), 3.88-3.42 (m, 2H, NCH$_2$), 3.84 (s, 3H$_2$OCH$_3$), 3.21-2.92 (m, 2H, C$_5$H$_{10}$), 2.32-2.09 (m, 2H, C$_5$H$_{10}$), 1.82-1.59 (m, 2H, C$_5$H$_{10}$), 1.60-1.40 (m, 2H, CH$_2$CH$_3$), 1.02 (t, 3H, CH$_2$CH$_3$)

A part of the white crystals was sampled and mass spectrometric analysis was carried out using ESI-MS (ZND, Micromass Inc.). The measured value was 307.1. These results confirm that the obtained white crystals were hydroxyl-containing amine imide B, i.e., 1-(2-hydroxybutyl)-1-(2-methoxybenzoyl)aminopiperidinium inner salt.

[Preparation of Hydroxyl-Containing Amine Imide C]

19.62 g (0.10 mol) of methyl 2,4-dimethoxybenzoate, 6.01 g (0.10 mol) of N,N-dimethylhydrazine, and 7.21 g (0.10 mol) of 1,2-epoxybutane were dissolved in 100 mL of isopropyl alcohol. The solution was reacted under stirring at room temperature for 6 days. After the reaction was completed, the solution was condensed in vacuo to remove the solvent and by-product methanol to give a viscous condensate. The viscous condensate was dissolved in 2 volumes of ethyl acetate. The solution was purified on a column packed with NH-silica gel (Fuji Silysia Chemical Ltd.) eluting with methanol/ethyl acetate (1:10). The purified product was dried in vacuo to give 5.80 g of transparent oily material with 98.0% purity (yield: 19.2 mol %).

A part of the white crystals was sampled and $^1$H-NMR characterization was carried out on JEOL EXcalibur270 spectrometer (25° C., CDCl$_3$, 270 MHz) to identify the crystal structure:

7.69 (d, 1H, C$_6$H$_3$), 6.95-6.87 (m, 2H, C$_6$H$_3$), 4.24-4.05 (m, 1H, CHOH), 3.83 (s, 6H$_2$OCH$_3$), 3.60 (d, 6H, NCH$_3$), 3.52-3.07 (m, 2H, NCH$_2$), 1.60-1.48 (m, 2H, CH$_2$CH$_3$), 1.02 (t, 3H, CH$_2$CH$_3$)

A part of the white crystals was sampled and mass spectrometric analysis was carried out using ESI-MS (ZND, Micromass Inc.). The measured value was 297.2. These results confirm that the obtained white crystals were hydroxyl-containing amine imide C, i.e., 1,1-dimethyl-1-(2-hydroxybutyl)amine o,p-dimethoxybenzimide.

[Preparation of Hydroxy-Containing Amine Imide D]

17.13 g (0.10 mol) of methyl 2-methoxybenzoate, 11.06 g (0.10 mol) of N-aminomorpholine, and 7.21 g (0.10 mol) of 1,2-epoxybutane were dissolved in 100 mL of t-butanol. The solution was reacted under stirring at 60° C. for 33 hours. After the reaction was completed, the solution was condensed to remove the solvent to give a viscous condensate. The viscous condensate was purified on a column packed with NH-silica gel (Fuji Silysia Chemical Ltd.) eluting with methanol/ethyl acetate (1:10). The purified product was crystallized using hexane and dried in vacuo to give 6.17 g of white crystals with 98.6% purity (yield: 19.7 mol %).

A part of the white crystals was sampled and $^1$H-NMR characterization was carried out on JEOL EXcalibur270 spectrometer (25° C., CDCl$_3$, 270 MHz) to identify the crystal structure:

7.43 (d, 1H, C$_6$H$_4$), 7.30-7.17 (m, 1H, C$_6$H$_4$), 6.96-6.81 (m, 2H, C$_6$H$_4$), 4.61-4.51 (m, 4H, C$_4$H$_8$O), 4.34-4.20 (m, 1H, CHOH), 3.87-3.42 (m, 2H, NCH$_2$), 3.83 (s, 3H$_2$OCH$_3$), 3.21-2.91 (m, 4H, C$_4$H$_8$O), 1.58-1.40 (m, 2H, CH$_2$CH$_3$), 1.02 (t, 3H, CH$_2$CH$_3$)

A part of the white crystals was sampled and mass spectrometric analysis was carried out using ESI-MS (ZND, Micromass Inc.). The measured value was 309.2. These results confirm that the obtained white crystals were hydroxyl-containing amine imide D, i.e., N-(2-hydroxybutyl)-N-(2-methoxybenzoyl)aminomorphonium inner salt.

[Preparation of Hydroxyl-Containing Amine Imide E]

19.62 g (0.10 mol) of methyl 2,4-dimethoxybenzoate, 10.96 g (0.10 mol) of 1-aminopiperidine, and 7.21 g (0.10 mol) of 1,2-epoxybutane were dissolved in 100 mL of t-butanol. The solution was reacted under stirring at 60° C. for 33 hours. After the reaction was completed, the solution was condensed to remove the solvent to give a viscous condensate. The viscous condensate was purified on a column packed with NH-silica gel (Fuji Silysia Chemical Ltd.) eluting with methanol/ethyl acetate (1:10). The purified product was washed with ethyl acetate/hexane (1:1) and dried in vacuo to give 11.43 g of white crystals with 99.0% purity (yield: 33.6 mol %).

A part of the white crystals was sampled and $^1$H-NMR characterization was carried out on JEOL EXcalibur270 spectrometer (25° C., CDCl$_3$, 270 MHz) to identify the crystal structure:

7.39 (d, 1H, C$_6$H$_3$), 6.97-6.82 (m, 2H, C$_6$H$_3$), 4.89-4.74 (m, 2H, C$_5$H$_{10}$), 4.64-4.51 (m, 2H, C$_5$H$_{10}$), 4.34-4.20 (m, 1H, CHOH), 3.87-3.42 (m, 2H, NCH$_2$), 3.83 (s, 6H$_2$OCH$_3$), 3.21-2.93 (m, 2H, C$_5$H$_{10}$), 2.33-2.09 (m, 2H, C$_5$H$_o$), 1.82-1.59 (m, 2H, C$_5$H$_{10}$), 1.58-1.40 (m, 2H, CH$_2$CH$_3$), 1.03 (t, 3H, CH$_2$CH$_3$)

A part of the white crystals was sampled and mass spectrometric analysis was carried out using ESI-MS (ZND, Micromass Inc.). The measured value was 337.2. These results confirm that the obtained white crystals were hydroxyl-containing amine imide E, i.e., 1-(2,4-dimethoxybenzoyl)amino-1-(2-hydroxybutyl)piperidinium inner salt.

[Preparation of Hydroxyl-Containing Amine Imide F]

10.21 g (0.10 mol) of ethyl propionate, 6.01 g (0.10 mol) of N,N-dimethylhydrazine, and 7.21 g (0.10 mol) of 1,2-epoxybutane were dissolved in 80 mL of t-butanol. The solution was reacted under stirring at 55° C. for 15 hours. After the reaction was completed, the solution was condensed in vacuo to remove the solvent and by-product ethanol to give a viscous condensate. The viscous condensate was crystallized using ethyl acetate and dried in vacuo to give 7.58 g of white crystals with 97.4% purity (yield: 39.2 mol %).

A part of the white crystals was sampled and $^1$H-NMR characterization was carried out on JEOL EXcalibur270 spectrometer (25° C., CDCl$_3$, 270 MHz) to identify the crystal structure:

7.11 (s, 1H$_2$OH), 4.16-4.07 (m, 1H, CH), 3.55 (s, 3H, NCH$_3$), 3.53 (s, 3H, NCH$_3$), 3.44-3.05 (m, 2H, NCH$_2$), 2.09-2.01 (q, 2H, COCH$_2$), 1.62-1.41 (m, 2H, CHCH$_2$), 1.10-1.05 (t, 3H, COCH$_2$CH$_3$), 1.05-0.99 (t, 3H, CH$_2$CH$_3$)

A part of the white crystals was sampled and mass spectrometric analysis was carried out using ESI-MS (ZND, Micromass Inc.). The measured value was 189.2. These results confirm that the obtained white crystals were hydroxyl-containing amine imide F, i.e., 1,1-dimethyl-1-(2-hydroxybutyl)aminoethylimide.

[Preparation of Hydroxyl-Containing Amine Imide G]

11.81 g (0.10 mol) of ethyl lactate, 6.01 g (0.10 mol) of N,N-dimethylhydrazine, and 7.21 g (0.10 mol) of 1,2-epoxybutane were dissolved in 80 mL of t-butanol. The solution was reacted under stirring at 55° C. for 13 hours. After the reaction was completed, the solution was condensed in vacuo to remove the solvent and by-product ethanol to give a viscous condensate. The viscous condensate was dissolved in 2 volumes of ethyl acetate. The solution was purified on a column packed with NH-silica gel (Fuji Silysia Chemical Ltd.) eluting with methanol/ethyl acetate (1:10). The purified product was dried in vacuo to give 17.57 g of transparent oily material with 99.6% purity (yield: 74.9 mol %).

A part of the white crystals was sampled and $^1$H-NMR characterization was carried out on JEOL EXcalibur270 spectrometer (25° C., CDCl$_3$, 270 MHz) to identify the crystal structure:

6.18 (s, 1H$_2$OH), 4.16-4.08 (m, 1H, COCH), 4.08-3.90 (m, 1H, CH$_2$CH), 3.83-3.26 (m, 2H, NCH$_2$), 3.54 (s, 3H, NCH$_3$), 3.52 (s, 3H, NCH$_3$), 1.67-1.41 (m, 2H, CHCH$_2$), 1.33-1.23 (m, 3H, CHCH$_3$), 1.06-0.98 (t, 3H, CH$_2$CH$_3$)

A part of the white crystals was sampled and mass spectrometric analysis was carried out using ESI-MS (ZND, Micromass Inc.). The measured value was 205.2. These results confirm that the obtained white crystals were hydroxyl-containing amine imide G, i.e., 1,1-dimethyl-1-(2-hydroxybutyl)amine lactamide.

[Preparation of Hydroxyl-Containing Amine Imide H]

16.42 g (0.10 mol) of ethyl 4-methylbenzoate, 6.01 g (0.10 mol) of N,N-dimethylhydrazine, and 7.21 g (0.10 mol) of 1,2-epoxybutane were dissolved in 80 mL of t-butanol. The solution was reacted under stirring at 55° C. for 14 hours. After the reaction was completed, the solution was condensed in vacuo to remove the solvent and by-product ethanol to give a viscous condensate. The viscous condensate was crystallized using hexane/ethyl acetate (1:1) and dried in vacuo to give 17.32 g of white crystals with 94.7% purity (yield: 65.5 mol %).

A part of the white crystals was sampled and $^1$H-NMR characterization was carried out on JEOL EXcalibur270 spectrometer (25° C., CDCl$_3$, 270 MHz) to identify the crystal structure:

7.74 (d, 2H, C$_6$H$_4$), 7.12 (d, 2H, C$_6$H$_4$), 4.24-4.16 (m, 1H, CHOH), 3.67 (d, 6H, NCH$_3$), 3.58-3.08 (m, 2H, NCH$_2$), 2.34 (s, 3H, C$_6$H$_4$CH$_3$), 1.70-1.42 (m, 2H, CH$_2$CH$_3$), 1.04 (t, 3H, CH$_2$CH$_3$)

A part of the white crystals was sampled and mass spectrometric analysis was carried out using ESI-MS (ZND, Micromass Inc.). The measured value was 251.3. These results confirm that the obtained white crystals were hydroxyl-containing amine imide H, i.e., 1,1-dimethyl-1-(2-hydroxybutyl)amine p-methylbenzamide.

[Preparation of Hydroxyl-Containing Amine Imide I]

16.82 g (0.10 mol) of ethyl 4-fluorobenzoate, 6.01 g (0.10 mol) of N,N-dimethylhydrazine, and 7.21 g (0.10 mol) of 1,2-epoxybutane were dissolved in 80 mL of t-butanol. The solution was reacted under stirring at 55° C. for 10 hours. After the reaction was completed, the solution was condensed in vacuo to remove the solvent and by-product ethanol to give a viscous condensate. The viscous condensate was crystallized using hexane/ethyl acetate (1:1) and dried in vacuo to give 17.44 g of white crystals with 97.2% purity (yield: 66.6 mol %).

A part of the white crystals was sampled and $^1$H-NMR characterization was carried out on JEOL EXcalibur270 spectrometer (25° C., CDCl$_3$, 270 MHz) to identify the crystal structure:

7.87-7.81 (m, 2H, C$_6$H$_4$), 7.02-6.95 (m, 2H, C$_6$H$_4$), 4.24-4.16 (m, 1H, CHOH), 3.67 (d, 6H, NCH$_3$), 3.59-3.13 (m, 2H, NCH$_2$), 1.67-1.45 (m, 2H, CH$_2$CH$_3$), 1.04 (t, 3H, CH$_2$CH$_3$)

A part of the white crystals was sampled and mass spectrometric analysis was carried out using ESI-MS (ZND, Micromass Inc.). The measured value was 255.2. These results confirm that the obtained white crystals were hydroxyl-containing amine imide I, i.e., 1,1-dimethyl-1-(2-hydroxybutyl)amine p-fluorobenzamide.

[Preparation of Hydroxyl-Containing Amine Imide J]

16.62 g (0.10 mol) of methyl 2-methoxybenzoate, 6.01 g (0.10 mol) of N,N-dimethylhydrazine, and 7.21 g (0.10 mol) of 1,2-epoxybutane were dissolved in 100 mL of isopropyl alcohol. The solution was reacted under stirring at room temperature for 3 days. After the reaction was completed, the solution was condensed in vacuo to remove the solvent and by-product methanol to give a viscous condensate. The viscous condensate was dissolved in 2 volumes of ethyl acetate. The solution was purified on a column packed with NH-silica gel (Fuji Silysia Chemical Ltd.) eluting with methanol/ethyl acetate (1:10). The purified product was dried in vacuo to give 12.12 g of transparent oily material with 96.8% purity (yield: 44.4 mol %).

A part of the white crystals was sampled and $^1$H-NMR characterization was carried out on JEOL EXcalibur270 spectrometer (25° C., CDCl$_3$, 270 MHz) to identify the crystal structure:

7.70 (d, 1H, C$_6$H$_4$), 7.29-7.24 (m, 1H, C$_6$H$_4$), 6.95-6.85 (m, 2H, C$_6$H$_4$), 4.27-4.05 (m, 1H, CHOH), 3.84 (s, 3H$_2$OCH$_3$), 3.65 (d, 6H, NCH$_3$), 3.56-3.01 (m, 2H, NCH$_2$), 1.60-1.48 (m, 2H, CH$_2$CH$_3$), 1.02 (t, 3H, CH$_2$CH$_3$)

A part of the white crystals was sampled and mass spectrometric analysis was carried out using ESI-MS (ZND, Micromass Inc.). The measured value was 266.0. These results confirm that the obtained white crystals were hydroxyl-containing amine imide J, i.e., 1,1-dimethyl-1-(2-hydroxybutyl)amine o-methoxybenzimide.

Hydroxyl-Containing Amine Imides A to J

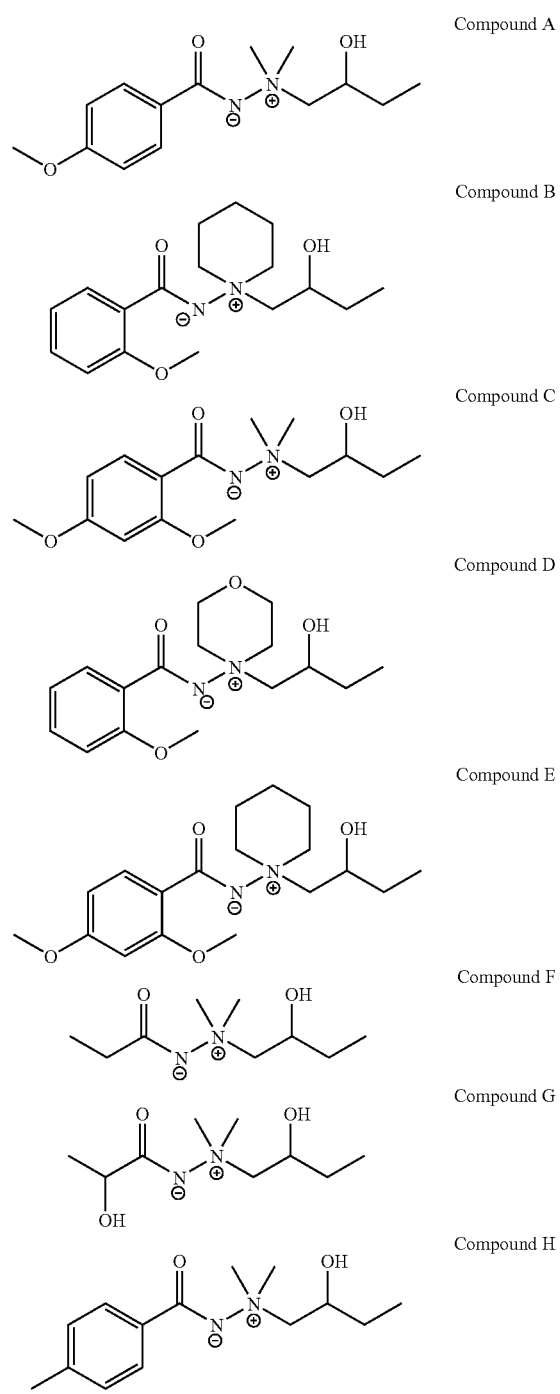

-continued

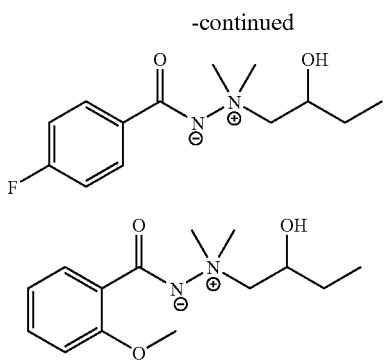

Compound I

Compound J

Synthesis Example 1

1.00 g (3.72 mmol) of Hydroxyl-containing amine imide A and 0.07 g (0.69 mmol) of triethylamine were dissolved in 10 ml of dichloromethane. To the mixture was added 0.66 g (5.58 mmol) of phenyl isocyanate and the solution was reacted under stirring at room temperature for 5 hours, to produce a homogeneous solution. The reaction solution was condensed in vacuo for solvent removal to yield a viscous condensate. The condensate was dissolved in ethyl acetate and was washed with water. The organic phase recovered during washing was condensed in vacuo to yield a viscous condensate. The condensate was dissolved in 2 volumes of ethyl acetate. The solution was purified twice on a column packed with NH-silica gel (Fuji Silysia Chemical Ltd.) eluting with methanol/ethyl acetate (1:10). The purified product was crystallized using hexane and dried in vacuo to give 0.67 g of white crystals with 99.0% purity (yield: 46.3 mol %).

A part of the white crystals was sampled and $^1$H-NMR characterization was carried out on JEOL EXcalibur270 spectrometer (25° C., CDCl$_3$, 270 MHz) to identify the crystal structure:

7.88 (d, 2H, C$_6$H$_4$), 7.34-7.02 (m, 5H, C$_6$H$_5$), 6.75 (d, 2H, C$_6$H$_4$), 5.44-5.39 (m, 1H, CHOH), 4.07-4.04 (m, 2H, NCH$_2$), 3.75 (s, 3H$_2$OCH$_3$), 3.45 (d, 6H, NCH$_3$), 1.75-1.65 (m, 2H, CH$_2$CH$_3$), 0.97 (t, 3H, CH$_2$CH$_3$)

A part of the white crystals was sampled and mass spectrometric analysis was carried out using ESI-MS (ZND, Micromass Inc.). The measured value was 386.2. These results confirm that the obtained white crystals were Amine imide 1, i.e., 1,1-dimethyl-1-(2-phenylcarbamylbutyl)amine p-methoxybenzimide.

Synthesis Example 2

6.36 g (24.0 mmol) of Hydroxyl-containing amine imide B and 0.40 g (4.0 mmol) of triethylamine were dissolved in 30 ml of dichloromethane. 3.57 g (30.0 mmol) of phenyl isocyanate was added dropwise at room temperature. The solution was reacted under stirring at room temperature for 10 hours. The reaction solution was condensed in vacuo for solvent removal to yield a viscous condensate. The viscous condensate was dissolved in ethyl acetate and washed with water to obtain an organic phase. The organic phase was condensed in vacuo to yield a viscous condensate. The condensate was dissolved in 2 volumes of ethyl acetate. The solution was purified twice on a column packed with NH-silica gel (Fuji Silysia Chemical Ltd.) eluting with methanol/ethyl acetate (1:10). The purified product was crystallized using hexane and dried in vacuo to give 7.04 g of white crystals with 97.2% purity (yield: 80.4 mol %).

A part of the white crystals was sampled and $^1$H-NMR characterization was carried out on JEOL EXcalibur270 spectrometer (25° C., CDCl$_3$, 270 MHz) to identify the crystal structure:

7.41-7.18 (m, 2H, C$_6$H$_4$), 7.41-7.02 (m, 5H, C$_6$H$_5$), 6.90-6.84 (m, 2H, C$_6$H$_4$), 4.92-4.80 (m, 2H, C$_5$H$_{10}$), 4.77-4.64 (m, 2H, C$_5$H$_{10}$), 4.17-4.04 (m, 1H, CHO), 4.00-3.60 (m, 2H, NCH$_2$), 3.84 (s, 3H$_2$OCH$_3$), 3.12-2.83 (m, 2H, C$_5$H$_o$), 2.49-2.20 (m, 2H, C$_5$H$_{10}$), 1.88-1.71 (m, 2H, C$_5$H$_{10}$), 1.71-1.56 (m, 2H, CH$_2$CH$_3$), 1.01 (t, 3H, CH$_2$CH$_3$)

A part of the white crystals was sampled and mass spectrometric analysis was carried out using ESI-MS (ZND, Micromass Inc.). The measured value was 426.1. These results confirm that the obtained white crystals were Amine imide 2, i.e., 1-(2-methoxybenzoyl)amino-1-(2-phenylcarbamoyloxybutyl)piperidinium inner salt.

Synthesis Example 3

2.82 g (9.04 mmol) of Hydroxyl-containing amine imide C and 0.18 g (1.78 mmol) of triethylamine were dissolved in 17 ml of dichloromethane. 1.65 g (13.6 mmol) of phenyl isocyanate was added at room temperature. The solution was reacted under stirring at 50° C. for 10 hours. The reaction solution was condensed in vacuo for solvent removal to yield a viscous condensate. The viscous condensate was purified on a column packed with NH-silica gel (Fuji Silysia Chemical Ltd.) eluting with methanol/ethyl acetate (1:10). The purified product was crystallized using hexane, washed with water, and dried to give 1.75 g of white crystals with 93.2% purity (yield: 49.1 mol %).

A part of the white crystals was sampled and $^1$H-NMR characterization was carried out on JEOL EXcalibur270 spectrometer (25° C., CDCl$_3$, 270 MHz) to identify the crystal structure:

7.41-7.25 (m, 1H, C$_6$H$_3$), 7.41-7.25 (m, 4H, C$_6$H$_5$), 7.08-7.03 (m, 1H, C$_6$H$_5$), 6.41-6.33 (m, 2H, C$_6$H$_3$), 4.17-4.11 (m, 1H, CHO), 3.83 (s, 3H$_2$OCH$_3$), 3.77 (s, 3H$_2$OCH$_3$), 3.37-3.28 (m, 2H, NCH$_2$), 2.04-2.02 (m, 3H, NCH$_3$), 1.80-1.69 (m, 3H, NCH$_3$), 1.28-1.23 (m, 2H, CH$_2$CH$_3$), 1.02-0.94 (m, 3H, CH$_2$CH$_3$)

A part of the white crystals was sampled and mass spectrometric analysis was carried out using ESI-MS (ZND, Micromass Inc.). The measured value was 416.2. These results confirm that the obtained white crystals were Amine imide 3, i.e., 1,1-dimethyl-1-(2-phenylcarbamylbutyl)amine o,p-dimethoxybenzimide.

Synthesis Example 4

4.69 g (15.0 mmol) of Hydroxyl-containing amine imide D and 0.30 g (3.0 mmol) of triethylamine were dissolved in 20 ml of dichloromethane. 2.43 g (20.0 mmol) of phenyl isocyanate was added at room temperature. The solution was reacted under stirring at room temperature for 12 hours. The reaction solution was condensed in vacuo for solvent removal to yield a viscous condensate. The viscous condensate was purified on a column packed with NH-silica gel (Fuji Silysia Chemical Ltd.) eluting with methanol/ethyl acetate (1:10). The purified product was crystallized using hexane and dried to give 5.08 g of white crystals with 98.6% purity (yield: 78.1 mol %).

A part of the white crystals was sampled and $^1$H-NMR characterization was carried out on JEOL EXcalibur270 spectrometer (25° C., CDCl$_3$, 270 MHz) to identify the crystal structure:

7.41-7.24 (m, 5H, $C_6H_5$), 7.39-6.92 (m, 4H, $C_6H_4$), 4.63-4.51 (m, 4H, $C_4H_8O$), 4.18-4.07 (m, 1H, CHO), 4.00-3.62 (m, 2H, $NCH_2$), 3.81 (s, $3H_2OCH_3$), 3.21-2.94 (m, 4H, $C_4H_8O$), 1.71-1.56 (m, 2H, $CH_2CH_3$), 1.01 (t, 3H, $CH_2CH_3$)

A part of the white crystals was sampled and mass spectrometric analysis was carried out using ESI-MS (ZND, Micromass Inc.). The measured value was 428.1. These results confirm that the obtained white crystals were Amine imide 4, i.e., N-(2-methoxybenzoyl)amino-N-(2-phenylcarbamoyloxybutyl)morpholinium inner salt.

Synthesis Example 5

8.50 g (25.0 mmol) of Hydroxyl-containing amine imide E and 0.51 g (5.1 mmol) of triethylamine were dissolved in 40 ml of dichloromethane. 4.01 g (33.0 mmol) of phenyl isocyanate was added at room temperature. The solution was reacted under stirring at room temperature for 3 days. The reaction solution was condensed in vacuo for solvent removal to yield a viscous condensate. The viscous condensate was purified on a column packed with NH-silica gel (Fuji Silysia Chemical Ltd.) eluting with methanol/ethyl acetate (1:10). The purified product was crystallized by condensation in vacuo using hexane, washed with water, and dried to give 10.91 g of white crystals with 98.2% purity (yield: 94.1 mol %).

A part of the white crystals was sampled and H-NMR characterization was carried out on JEOL EXcalibur270 spectrometer (25° C., $CDCl_3$, 270 MHz) to identify the crystal structure:

7.61-7.02 (m, 5H, $C_6H_5$), 7.59-6.84 (m, 3H, $C_6H_3$), 4.82-4.70 (m, 2H, $C_5H_{10}$), 4.67-4.60 (m, 2H, $C_5H_{10}$), 4.18-4.04 (m, 1H, CHO), 3.81-3.60 (m, 2H, $NCH_2$), 3.74 (s, $6H_2OCH_3$), 3.12-2.93 (m, 2H, $C_5H_{10}$), 2.55-2.32 (m, 2H, $C_5H_{10}$), 1.88-1.73 (m, 2H, $C_5H_{10}$), 1.67-1.56 (m, 2H, $CH_2CH_3$), 1.03 (t, 3H, $CH_2CH_3$)

A part of the white crystals was sampled and mass spectrometric analysis was carried out using ESI-MS (ZND, Micromass Inc.). The measured value was 456.2. These results confirm that the obtained white crystals were Amine imide 5, i.e., 1(2,4-dimethoxybenzoyl)amino-1-(2-pivaloyloxybutyl)piperidinium inner salt.

Synthesis Example 6

6.16 g (0.020 mol) of Hydroxyl-containing amine imide B and 2.98 g (0.028 mol) of acetic anhydride were dissolved in 19 ml of methyl ethyl ketone. The solution was reacted under stirring at 80° C. for 6 hours. The reaction solution was condensed in vacuo for removal of solvent and acetic acid to yield a viscous condensate. The viscous condensate was dissolved in ethyl acetate and extracted with water. The obtained aqueous phase was condensed in vacuo to yield a viscous condensate. Ethyl acetate was added to the viscous condensate. After condensed, the obtained slurry was washed with ethyl acetate. The obtained organic phase was condensed, crystallized using hexane, and dried in vacuo to give 3.74 g of white crystals with 99.2% purity (yield: 53.2 mol %).

A part of the white crystals was sampled and $^1$H-NMR characterization was carried out on JEOL EXcalibur270 spectrometer (25° C., $CDCl_3$, 270 MHz) to identify the crystal structure:

7.39-7.35 (m, 1H, $C_6H_4$), 7.24-7.18 (m, 1H, $C_6H_4$), 6.91-6.84 (m, 2H, $C_6H_4$), 5.67-5.65 (m, 1H, CHO), 4.98-4.90 (m, 2H, $NCH_2$), 3.84 (s, $3H_2OCH_3$), 3.78-3.74 (m, 1H, $C_5H_{10}$), 3.44-3.36 (m, 1H, $C_5H_{10}$), 3.14-3.06 (m, 1H, $C_5H_{10}$), 2.92-2.81 (m, 1H, $C_5H_o$), 2.39-2.26 (m, 2H, $C_5H_{10}$), 2.05 (s, 3H, $CH_3CO$), 1.83-1.36 (m, 6H, $C_5H_{10}$+$CH_2CH_3$), 0.96 (t, 3H, $CH_2CH_3$)

A part of the white crystals was sampled and mass spectrometric analysis was carried out using ESI-MS (ZND, Micromass Inc.). The measured value was 349.2. These results confirm that the obtained white crystals were Amine imide 6, i.e., 1-(2-acetoxybutyl)-1-(2-methoxybenzoyl)aminopiperidinium inner salt.

Synthesis Example 7

6.16 g (0.020 mol) of Hydroxyl-containing amine imide B and 6.53 g (0.028 mol) of benzoic anhydride were dissolved in 15 ml of methyl ethyl ketone. The solution was reacted under stirring at 80° C. for 2 hours. The reaction solution was condensed in vacuo for solvent removal to yield a viscous condensate. The viscous condensate was dissolved in 2 volumes of ethyl acetate and purified on a column packed with NH-silica gel (Fuji Silysia Chemical Ltd.) eluting with methanol/ethyl acetate (1:10). The purified product was crystallized using hexane and dried in vacuo to give 7.94 g of white crystals with 99.2% purity (yield: 75.9 mol %).

A part of the white crystals was sampled and $^1$H-NMR characterization was carried out on JEOL EXcalibur270 spectrometer (25° C., $CDCl_3$, 270 MHz) to identify the crystal structure:

8.05-8.02 (m, 2H, $C_6H_5$), 7.61-7.55 (m, 1H, $C_6H_5$), 7.48-7.38 (m, 3H, $C_5H_{10}$+$C_6H_4$), 7.27-7.19 (m, 1H, $C_6H_4$), 6.92-6.86 (m, 2H, $C_6H_4$), 5.95-5.93 (m, 1H, CHO), 5.14-4.94 (m, 2H, $NCH_2$), 3.87 (s, $3H_2OCH_3$), 3.80-3.76 (m, 1H, $C_5H_{10}$), 3.64-3.57 (m, 1H, $C_5H_{10}$), 3.15-3.14 (m, 1H, $C_5H_{10}$), 2.92-2.91 (m, 1H, $C_5H_{10}$), 2.39-2.27 (m, 2H, $C_5H_{10}$), 1.94-1.35 (m, 6H, $C_5H_{10}$+$CH_2CH_3$), 1.03 (t, 3H, $CH_2CH_3$)

A part of the white crystals was sampled and mass spectrometric analysis was carried out using ESI-MS (ZND, Micromass Inc.). The measured value was 411.3. These results confirm that the obtained white crystals were Amine imide 7, i.e., 1-(2-benzoyloxybutyl)-1-(2-methoxybenzoyl)aminopiperidinium inner salt.

Synthesis Example 8

3.06 g (0.010 mol) of Hydroxyl-containing amine imide B and 1.63 g (0.020 mol) of pyridine were dissolved in 10 ml of dichloromethane, and 1.81 g (0.015 mol) of pivaloyl chloride was added dropwise on ice. After addition, the solution was reacted under stirring at 50° C. for 7 hours. The reaction solution was condensed in vacuo for solvent removal to yield a viscous condensate. The viscous condensate was dissolved in dichloromethane and washed with water. The obtained organic phase was condensed in vacuo to yield a viscous condensate. The viscous condensate was dissolved in 2 volumes of ethyl acetate, crystallized using hexane, and dried in vacuo to give 2.71 g of white crystals with 99.8% purity (yield: 69.4 mol %).

A part of the white crystals was sampled and $^1$H-NMR characterization was carried out on JEOL EXcalibur270 spectrometer (25° C., $CDCl_3$, 270 MHz) to identify the crystal structure:

7.38-7.35 (m, 1H, $C_6H_4$), 7.27-7.18 (m, 1H, $C_6H_4$), 6.91-6.85 (m, 2H, $C_6H_4$), 5.67-5.65 (m, 1H, CHO), 5.07-4.87 (m, 2H, $NCH_2$), 3.85 (s, $3H_2OCH_3$), 3.71-3.67 (m, 1H, $C_5H_{10}$), 3.45-3.37 (m, 1H, $C_5H_{10}$), 3.18-3.106 (m, 1H, $C_5H_{10}$), 2.89-2.81 (m, 1H, $C_5H_{10}$), 2.38-2.25 (m, 2H, $C_5H_{10}$), 1.82-1.41 (m, 6H, $C_5H_{10}$+$CH_2CH_3$), 1.20 (s, 9H, $C(CH_3)_3$), 0.96 (t, 3H, $CH_2CH_3$)

A part of the white crystals was sampled and mass spectrometric analysis was carried out using ESI-MS (ZND, Micromass Inc.). The measured value was 391.3. These results confirm that the obtained white crystals were Amine imide 8, i.e., 1-(2-methoxybenzoyl)amino-1-(2-pivaloyloxybutyl)piperidinium inner salt.

Synthesis Example 9

1.74 g (0.0065 mol) of Hydroxyl-containing amine imide J and 5.94 g (0.075 mol) of pyridine were dissolved in 15 ml of dichloromethane, and 3.39 g (0.028 mol) of pivaloyl chloride was added dropwise on ice. After addition, the solution was reacted under stirring at room temperature for 70 hours. The reaction solution was condensed in vacuo for solvent removal to yield a viscous condensate. The viscous condensate was dissolved in 2 volumes of ethyl acetate and purified on a column packed with NH-silica gel (Fuji Silysia Chemical Ltd.) eluting with methanol/ethyl acetate (1:10). The purified product was crystallized using hexane and dried in vacuo to give 0.82 g of white crystals with 98.1% purity (yield: 36.0 mol %)

A part of the white crystals was sampled and $^1$H-NMR characterization was carried out on JEOL EXcalibur270 spectrometer (25° C., CDCl$_3$, 270 MHz) to identify the crystal structure:

7.49-7.43 (m, 2H, C$_6$H$_4$), 7.12-6.98 (m, 2H, C$_6$H$_4$), 5.61-5.53 (m, 1H, CH), 4.92-4.70 (m, 2H, NCH$_2$), 3.95 (s, 3H$_2$OCH$_3$), 3.71 (s, 2H, NCH$_3$), 3.40 (s, 2H, NCH$_3$), 1.80-1.60 (m, 2H, CH$_2$CH$_3$), 1.21 (s, 9H, C(CH$_3$)$_3$), 0.96 (t, 3H, CH$_2$CH$_3$)

A part of the white crystals was sampled and mass spectrometric analysis was carried out using ESI-MS (ZND, Micromass Inc.). The measured value was 351.3. These results confirm that the obtained white crystals were Amine imide 9, i.e., 1,1-dimethyl-1-(2-pivaloyloxybutyl)amine o-methoxybenzimide.

Synthesis Example 10

4.56 g (0.0149 mol) of Hydroxyl-containing amine imide B and 1.976 g of pyridine were dissolved in 60 ml of ethyl acetate, and 7.76 g (0.0455 mol) of 2-methoxybenzoyl chloride was added dropwise on ice. After addition, the solution was reacted under stirring at 50° C. for 7 hours.

After cooling the reaction solution, the precipitated solid was dissolved by the addition of sodium bicarbonate water and ethyl acetate. The obtained organic phase was washed with water and dried over magnesium sulfate. After removing the desiccant by filtration, the organic phase was condensed in vacuo, and the obtained residue was crystallized using ethyl acetate to yield 4.15 g of white crystals of 1-(2-methoxybenzoyl)amino-1-[2-(2-methoxybenzoyloxy)butyl]piperidinium inner salt (yield: 63.2 mol %).

A part of the white crystals was sampled and $^1$H-NMR characterization was carried out on JEOL EXcalibur270 spectrometer (25° C., CDCl$_3$, 270 MHz) to identify the crystal structure:

δ (ppm) 7.76 (d, 1H, J=2.6 Hz), 7.516-7.451 (m, 1H), 7.40 (dd, 1H, J=2.8 Hz), 7.26-7.19 (m, 1H), 7.02-6.96 (m, 2H), 5.87 (q, 1H, J=6 Hz), 5.05 (dd, 1H, J=1 Hz, 14 Hz), 4.95 (br.d, 1H), 3.87 (d, 7H, J=5 Hz), 3.59 (q, 1H, J=7.7 Hz), 3.12 (dt, 1H, J=9 Hz, 11 Hz), 2.95 (dt, 1H, J=3 Hz, 12 Hz), 2.48-2.22 (m, 1H), 1.97-1.84 (m, 2H), 1.82-1.71 (m, 1H), 1.80-1.52 (m, 3H), 1.50-1.31 (m, 1H), 1.04 (t, 3H, J=8 Hz)

A part of the white crystals was sampled and mass spectrometric analysis was carried out using ESI-MS (ZND, Micromass Inc.). In the mass spectrum, a patent peak was observed which corresponds to Amine imide 10, i.e., 1-(2-methoxybenzoyl)amino-1-[2-(2-methoxybenzoyloxy)butyl] piperidinium inner salt.

Synthesis Example 11

4.6 g (0.015 mol) of Hydroxyl-containing amine imide B and 2.34 g of pyridine were dissolved in 60 ml of ethyl acetate, and 4.85 g (0.0314 mol) of 2-methylbenzoyl chloride was added dropwise thereto on ice. After addition, the solution was reacted under stirring at 50° C. for 7 hours. After cooling the reaction solution, the precipitated solid was dissolved by the addition of sodium bicarbonate water and ethyl acetate. The obtained organic phase was washed with water and dried over magnesium sulfate. After removing the desiccant by filtration, the organic phase was condensed in vacuo, and the obtained residue was crystallized using ethyl acetate/hexane mixture to yield 3.62 g of white crystals of 1-(2-methoxybenzoyl)amino-1-[2-(2-methylbenzoyloxy)butyl] piperidinium inner salt (yield: 56.7 mol %).

A part of the white crystals was sampled and $^1$H-NMR characterization was carried out on JEOL EXcalibur270 spectrometer (25° C., CDCl$_3$, 270 MHz) to identify the crystal structure:

δ (ppm) 7.89 (d, 1H, J=9 Hz), 7.45-7.38 (m, 2H), 7.27-7.19 (m, 3H), 6.92-6.86 (m, 2H), 5.90 (q, 1H, J=6 Hz), 5.10 (dd, 1H, J=1.4 Hz, 14 Hz), 4.98 (br.d, 1H), 3.87 (s, 3H), 3.79 (br.d, 1H), 3.57 (q, 1H, J=7 Hz), 3.11 (dt, 1H, J=3 Hz, 12 Hz), 2.91 (dt, 1H, J=3 Hz, 12 Hz), 2.61 (s, 3H), 2.45-2.20 (m, 2H), 2.00-1.80 (m, 2H), 1.80-1.50 (m, 3H), 1.50-1.30 (m, 1H), 1.05 (t, 3H, J=7.5 Hz)

A part of the white crystals was sampled and mass spectrometric analysis was carried out using ESI-MS (ZND, Micromass Inc.). In the mass spectrum, a patent peak was observed which corresponds to Amine imide 11, i.e., 1-(2-methoxybenzoyl)amino-1-[2-(2-methylbenzoyloxy)butyl] piperidinium inner salt.

Amine imides 1 to 11 used in the present invention are shown below.

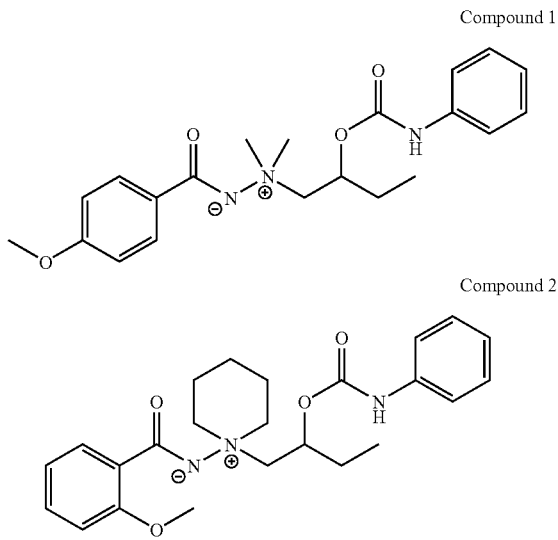

Compound 1

Compound 2

-continued

Compound 3
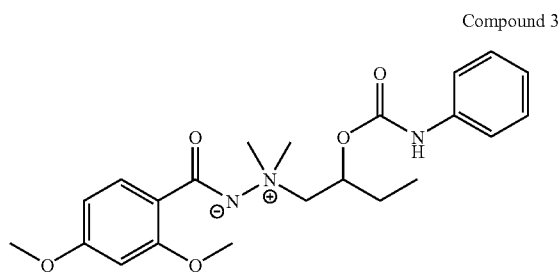

Compound 4
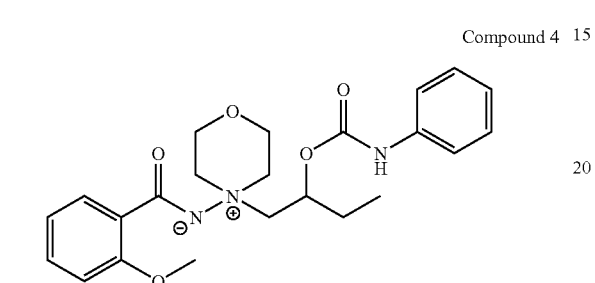

Compound 5
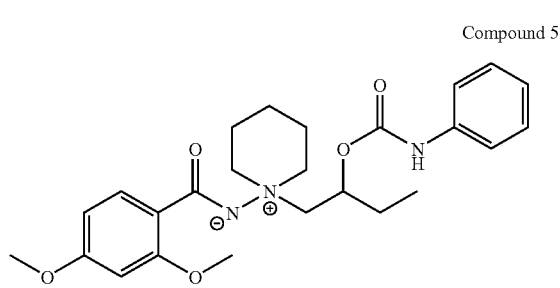

Compound 6
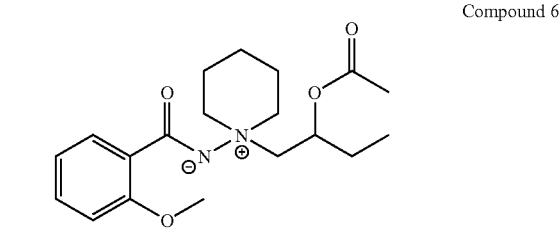

Compound 7
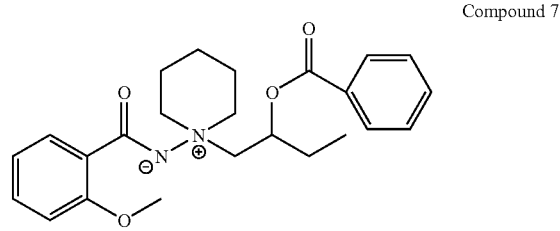

Compound 8
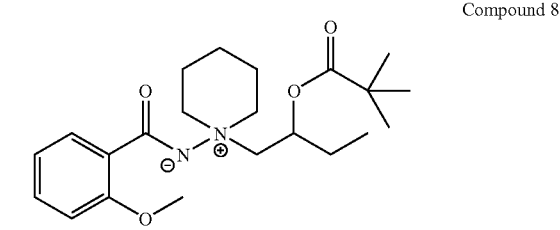

Compound 9
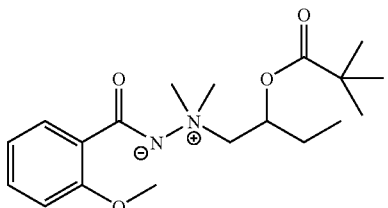

Compound 10
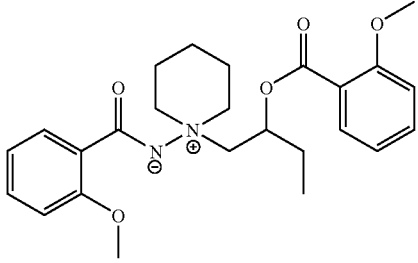

Compound 11
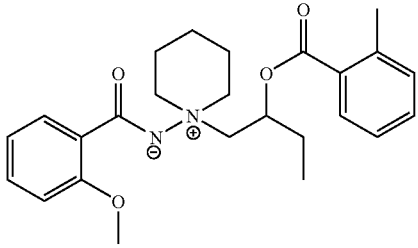

Epoxy resin compositions containing an amine imide according to the present invention or a hydroxyl-containing amine imide were prepared, and evaluated for their properties—curing ability, room temperature storage stability, and initial viscosity.

[Preparation of Epoxy Resin Compositions]

Epoxy resin compositions according to Examples and Comparative Examples were prepared from the raw materials described below. When mixing the raw materials, the equivalent ratio of acid anhydride to epoxy resin was set to 1 and an amine imide was used in an amount of "0.037×molecular weight parts by weight" per 100 parts by weight of the epoxy resin. The epoxy resin composition was prepared as follows: A corresponding amine imide and acid anhydride were charged into a mixer and mixed for 8 hours at 25° C., dissolving the amine imide into the acid anhydride, and a predetermined amount of epoxy resin was added and further mixed at 25° C. for 1 hour.

Epoxy resin (EPICLON 830S, Dainippon Ink and Chemicals, Inc.): 100 parts by weight Acid anhydride (RIKACID MH-700, New Japan Chemical Co., Ltd.): 93 parts by weight Amine imide of corresponding Example or Comparative Example: (molecular weight)×0.037 parts by weight

[Curing Ability]

Samples were prepared in which the epoxy resin composition is sandwiched between two 5-mm-thick NaCl crystal plates. Each sample was measured for its infrared transmission spectra with an FT-IR spectrometer, before and after a 2-hour heat treatment at 90° C. In each IR spectrum the height of an absorption peak caused by asymmetric stretching vibrations of the epoxy group (near 910 cm$^{-1}$) is divided by the height of an absorption peak caused by in-plane C—C stretching vibrations of the benzene ring (near 1,600 cm$^{-1}$) to standardize the value for the absorption peak derived from the epoxy group. The reaction ratio of epoxy groups was then calculated based on the attenuation level of the epoxy group-derived absorption peak due to heat treatment.

Epoxy conversion ratio was calculated using the equation $[(x1-x2/x1)\times 100(\%)]$, where x1 is the value standardized for the epoxy-derived absorption peak before heat treatment of the epoxy resin composition, and x2 is the value standardized for the epoxy-derived absorption peak after a 2-hour heat treatment at predetermined temperature. The more the value of epoxy conversion ratio is close to 100%, the more the epoxy groups have been consumed and the farther curing has proceeded. The epoxy resin compositions were evaluated for their epoxy conversion ratio based on the following criteria:

○: Epoxy conversion ratio=90 to 100%; extremely high curing ability

Δ: Epoxy conversion ratio=50 to less than 90%; high curing ability x: Epoxy conversion ratio=0 to less than 50%; poor curing ability

[Room Temperature Storage Stability]

Viscosity changes expressed as $\eta 2/\eta 1$ were calculated, where is viscosity of the epoxy resin composition at room temperature, and $\eta 2$ is viscosity of the epoxy resin composition after being allowed to stand for 24 hours at room temperature. The epoxy resin compositions were evaluated for their room temperature storage stability based on the following criteria:

○: $\eta 2/\eta 1$=less than 1.5; extremely high storage stability

Δ: $\eta 2/\eta 1$=1.5 to less than 2.0; high storage stability x: $\eta 2/\eta 1$=2.0 or more; poor storage stability

[Initial Viscosity]

The epoxy resin compositions were measured for their viscosity with an E-type viscometer (RC-500, Toki Sangyo Co., Ltd.) at 25° C. for 3 minutes. The obtained value was defined as initial viscosity (mPa·s) of the epoxy resin composition.

[Dissociation Ability of Amine Imide: N—N Bond Energy]

Values for the N—N bond energy in the amine imides were calculated by the "B3LYP method" known as a density functional theory. As a calculation program, Gaussian 03 Rev. C. 02 was used. As basis functions, the cc-pVDZ basis set was used for every element.

More specifically, the amine imide dissociation reaction represented by the above-described Scheme A was assumed, and the chemical structures of the reactant and products in Scheme A were optimized, followed by calculation of the total energy of each of the compounds. The value of the total energy of the amine imide prior to dissociation was subtracted from the value of the sum of the total energies of the products obtained by dissociation, to find a value of N—N bond energy.

Example 1

An epoxy resin composition was prepared using Amine imide 1 prepared in Synthesis Example 1 and evaluated for its properties.

Example 2

An epoxy resin composition was prepared and evaluated for its properties in the same manner as in Example 1 except that Amine imide 1 was replaced by Amine imide 2 prepared in Synthesis Example 2.

Example 3

An epoxy resin composition was prepared and evaluated for its properties in the same manner as in Example 1 except that Amine imide 1 was replaced by Amine imide 3 prepared in Synthesis Example 3.

Example 4

An epoxy resin composition was prepared and evaluated for its properties in the same manner as in Example 1 except that Amine imide 1 was replaced by Amine imide 4 prepared in Synthesis Example 4.

Example 5

An epoxy resin composition was prepared and evaluated for its properties in the same manner as in Example 1 except that Amine imide 1 was replaced by Amine imide 5 prepared in Synthesis Example 5.

Example 6

An epoxy resin composition was prepared and evaluated for its properties in the same manner as in Example 1 except that Amine imide 1 was replaced by Amine imide 6 prepared in Synthesis Example 6.

Example 7

An epoxy resin composition was prepared and evaluated for its properties in the same manner as in Example 1 except that Amine imide 1 was replaced by Amine imide 7 prepared in Synthesis Example 7.

Example 8

An epoxy resin composition was prepared and evaluated for its properties in the same manner as in Example 1 except that Amine imide 1 was replaced by Amine imide 8 prepared in Synthesis Example 8.

Example 9

An epoxy resin composition was prepared and evaluated for its properties in the same manner as in Example 1 except that Amine imide 1 was replaced by Amine imide 9 prepared in Synthesis Example 9.

Comparative Example 1

An epoxy resin composition was prepared and evaluated for its properties in the same manner as in Example 1 except that Amine imide 1 was replaced by Hydroxyl-containing amine imide A.

Comparative Example 2

An epoxy resin composition was prepared and evaluated for its properties in the same manner as in Example 1 except that Amine imide 1 was replaced by Hydroxyl-containing amine imide B.

Comparative Example 3

An epoxy resin composition was prepared and evaluated for its properties in the same manner as in Example 1 except that Amine imide 1 was replaced by Hydroxyl-containing amine imide F.

Comparative Example 4

An epoxy resin composition was prepared and evaluated for its properties in the same manner as in Example 1 except that Amine imide 1 was replaced by Hydroxyl-containing amine imide G.

Comparative Example 5

An epoxy resin composition was prepared and evaluated for its properties in the same manner as in Example 1 except that Amine imide 1 was replaced by Hydroxyl-containing amine imide H.

Comparative Example 6

An epoxy resin composition was prepared and evaluated for its properties in the same manner as in Example 1 except that Amine imide 1 was replaced by Hydroxyl-containing amine imide I.

Comparative Example 7

An epoxy resin composition was prepared and evaluated for its properties in the same manner as in Example 1 except that Amine imide 1 was replaced by Hydroxyl-containing amine imide C.

Comparative Example 8

An epoxy resin composition was prepared and evaluated for its properties in the same manner as in Example 1 except that Amine imide 1 was replaced by Hydroxyl-containing amine imide J.

Measurements of properties (curing ability, room temperature storage stability, initial viscosity, and N—N bond energy) of the epoxy resin compositions of Examples 1 to 9 and Comparative Examples 1 to 8 are shown in Tables 1-1 and 1-2 in FIG. 1.

As can be seen in Table 1-1, the epoxy resin compositions of Examples 1 to 9, which are free from such highly reactive organic groups as hydroxyl groups, cure at low temperatures around 90° C. and exhibit high room temperature storage stability. Moreover, these epoxy resin compositions have low initial viscosity and thus are easy to handle.

On the other hand, some of the epoxy resin compositions of Comparative Examples 1 to 8 exhibit high low-temperature curing ability, as shown in Table 1-2. However, these epoxy resin compositions exhibit low room temperature storage stability due to the presence of hydroxyl-containing amine imides. Moreover, they exhibit high initial viscosity and thus are less easy to handle. Thus, the epoxy resin compositions of Comparative Examples 1 to 8 lack balance in respect of low-temperature curing ability, room temperature storage stability, and initial viscosity.

This can be more clearly understood by comparing Example 1 and Comparative Example 1 as well as Example 2 and Comparative Example 2. It appears that high values for low-temperature curing ability of the epoxy resin compositions of Examples 1 to 9 are due to small N—N bond energy in the amine imide, a component of the epoxy resin composition.

Specifically, values for the N—N bond energy in the amine imides of Examples and Comparative Examples were calculated and compared to evaluate the dissociation ability of the amine imides. Also as shown in Table 1-1, values for the N—N bond energy in the amine imides in Examples 1 to 9 range from around 210 kJ/mol at maximum to less than 112 kJ/mol at minimum. Thus, the amine imides of Examples 1 to 9 are extremely low in N—N bond energy.

By contrast, values for the N—N bond energy in the amine imides of Comparative Examples 1 to 8 are not less than 175 kJ/mol; many of them exceed 210 kJ/mol. Thus, the amine imides of Comparative Examples 1 to 8 are relatively high in N—N bond energy.

Further, comparison between Examples 1 and 3 reveals that N—N bond energy is lower (i.e., low-temperature curing ability increases) when a substituent is attached to the ortho and para positions on the phenyl group bonded to the carbonyl carbon atom of the amine imide as compared to when a substituent is attached only to the para position of that phenyl group. Comparison between Examples 2 and 5 similarly reveals that N—N bond energy is lower (i.e., low-temperature curing ability increases) when a substituent is attached to the ortho and para positions on the phenyl group bonded to the carbonyl carbon atom of the amine imide as compared to when a substituent is attached only to the ortho position of that phenyl group.

Comparison between Examples 3 and 5 or Examples 8 and 9 further reveal that lower N—N bond energy result in higher low-temperature curing ability.

Comparison between Example 2 and Examples 6 to 8 also reveal that epoxy resin compositions containing an amine imide in which $R^5$ is acyl group show a better balance between room temperature storage stability and low-temperature curing ability than do epoxy resin compositions containing an amine imide in which $R^5$ is N-substituted aminocarbonyl group.

The epoxy resin compositions of Examples 1 to 5 were measured for their low-temperature curing ability at 80° C. While the epoxy conversion ratio of the epoxy resin composition of Example 1 was somewhat low, the epoxy conversion ratios of the epoxy resin compositions of Examples 2 to 5 were 83.8%, 70.0%, 79.8% and 81.9%, respectively, offering high curing ability at 80° C.

The present application claims the priority of Japanese Patent Application No. 2007-340785 filed on Dec. 28, 2007, the entire contents of which are herein incorporated by reference.

INDUSTRIAL APPLICABILITY

The amine imides used in the present invention have a relatively unstable N—N bond in their molecular structure and thus are readily dissociated at low temperatures to produce an isocyanate and a tertiary amine. Thus, the amine imides are useful as a curing agent for curing ionically polymerizable compounds such as epoxy resins.

Moreover, epoxy resin compositions which contain the amine imide used in the present invention, epoxy resin and acid anhydride have high room temperature storage stability and fully cure at low temperatures. Thus, the amine imides used in the present invention may provide epoxy resin compositions tailored to various applications, including sealants for organic EL displays.

The invention claimed is:

1. An epoxy resin composition comprising (a) a latent curing agent and (b) an epoxy resin, wherein:

(a) the latent curing agent is for curing (b) the epoxy resin, and comprises a hydroxyl-free amine imide having the following general formula (1):

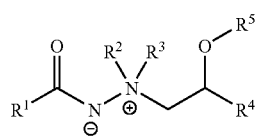

(1)

where $R^1$ and $R^4$ each denote an organic group and are the same or different; $R^2$ and $R^3$ independently denote a non-substituted or substituted alkyl or aryl group or are joined together to form a ring; $R^5$ denotes an organic group; and none of $R^1$ to $R^5$ has an organic group reactive with (b) the epoxy resin, and having an N—N bond energy of 100 to 210 kJ/mol as determined by the B3LYP density functional method.

2. The epoxy resin composition according to claim 1, wherein $R^1$ in general formula (1) is a non-substituted or substituted aryl or aryloxy group.

3. The epoxy resin composition according to claim 1, wherein $R^2$ and $R^3$ in general formula (1) are joined together to form a divalent saturated hydrocarbon having 4 to 8 carbon atoms, a moiety having the formula —$(CH_2)_n O(CH_2)_n$—, or a moiety having the formula —$(CH_2)_n NR^{11}(CH_2)_n$— (where n is a natural number of 2 to 4, and $R^{11}$ is any organic group).

4. The epoxy resin composition according to claim 1, wherein $R^5$ in general formula (1) is an organic group having a carbonyl group, and the carbon atom of the carbonyl group is bonded to an oxygen atom in general formula (1).

5. The epoxy resin composition according to claim 1, wherein $R^5$ in general formula (1) is an acyl group.

6. The epoxy resin composition according to claim 1, further comprising (c) an acid anhydride.

7. The epoxy resin composition according to claim 6, wherein the equivalent ratio of acid anhydride group to epoxy group is 0.8 to 1.2, and the mole ratio of amine imide group to epoxy group is 0.008 to 0.152.

8. The epoxy resin composition according to claim 1, wherein the amine imide has an N—N bond energy of 100 to 195 kJ/mol.

* * * * *